United States Patent [19]

Takiguchi et al.

[11] Patent Number: 5,318,720
[45] Date of Patent: Jun. 7, 1994

[54] LIQUID CRYSTAL COMPOSITION, LIQUID CRYSTAL DEVICE, DISPLAY APPARATUS AND DISPLAY METHOD

[75] Inventors: Takao Takiguchi, Tokyo; Takashi Iwaki, Machida; Takeshi Togano, Yokohama; Yoko Yamada; Shinichi Nakamura, both of Atsugi, all of Japan

[73] Assignee: Canon Kabushiki Kaisha, Tokyo, Japan

[21] Appl. No.: 711,061

[22] Filed: Jun. 6, 1991

[30] Foreign Application Priority Data

Jun. 8, 1990 [JP]  Japan .................................. 2-150130

[51] Int. Cl.$^5$ .................... C09K 19/34; C07D 261/04
[52] U.S. Cl. ............................ 252/299.61; 548/244; 359/76; 359/104; 359/106
[58] Field of Search ................... 252/299.01, 299.61; 359/76, 104, 106; 548/244

[56] References Cited

U.S. PATENT DOCUMENTS

| | | | |
|---|---|---|---|
| 4,367,924 | 1/1983 | Clark et al. | 350/334 |
| 5,034,151 | 7/1991 | Shinjo et al. | 252/299.6 |
| 5,244,596 | 9/1993 | Takiguchi et al. | 252/299.61 |

FOREIGN PATENT DOCUMENTS

| | | |
|---|---|---|
| 0005188 | 4/1979 | European Pat. Off. |
| 0002920 | 7/1979 | European Pat. Off. |
| 2619547 | 11/1977 | Fed. Rep. of Germany |
| 56-107216 | 8/1981 | Japan |
| 287947 | 12/1971 | U.S.S.R. |

OTHER PUBLICATIONS

Pavluchenko et al., Mol. Cryst. Liq. Cryst., vol. 37, pp. 35–46, (1976).
Schadt et al. "Applied Physics Letter," vol. 18, No. 4 pp. 127–128 (1971).
Chemical Abstracts of Japan, vol. 87, No. 1 (Jul. 4, 1977) 4816q.
Chemical Abstracts of Japan, vol. 98, No. 21 (May 23, 1983) 179360r.
Chemical Abstracts of Japan, vol. 106, No. 8 (Feb. 23, 1987) 51685s.
Chemical Abstracts of Japan, vol. 72, No. 1 (Jan. 5, 1970) 3475f.
Chemical Abstracts of Japan, vol. 110, No. 20 (May 15, 1989) 174690e.
Chemical Abstracts of Japan, vol. 113, No. 3, (Jul. 16, 1990) 20797v.

*Primary Examiner*—Philip Tucker
*Attorney, Agent, or Firm*—Fitzpatrick, Cella, Harper & Scinto

[57] ABSTRACT

A mesomorphic compound represented by the following formula (I):

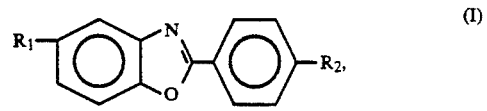

(I)

wherein $R_1$ and $R_2$ respectively denote an alkyl group or alkoxy group each having 4–16 carbon atoms optionally substituted, halogen, —CN or —CF$_3$. The mesomorphic compound is effective for providing a ferroelectric liquid crystal composition showing an improved low-temperature operation characteristic and a decreased temperature-dependence of response speed.

16 Claims, 4 Drawing Sheets

LIQUID CRYSTAL COMPOSITION, LIQUID CRYSTAL DEVICE, DISPLAY APPARATUS AND DISPLAY METHOD

FIELD OF THE INVENTION AND RELATED ART

The present invention relates to a novel mesomorphic compound, a liquid crystal composition, a liquid crystal device, a display apparatus and a display method, and more particularly to a novel mesomorphic compound and a liquid crystal composition with improved responsiveness to an electric field, a liquid crystal device using the liquid crystal composition for use in a display device, a liquid crystal-optical shutter, etc., a display apparatus using the device, and a display method using the composition and device.

Hitherto, liquid crystal devices have been used as an electro-optical device in various fields. Most liquid crystal devices which have been put into practice use TN (twisted nematic) type liquid crystals, as shown in "Voltage-Dependent Optical Activity of a Twisted Nematic Liquid Crystal" by M. Schadt and W. Helfrich "Applied Physics Letters" Vol. 18, No. 4 (Feb. 15, 1971) pp. 127–128.

These devices are based on the dielectric alignment effect of a liquid crystal and utilize an effect that the average molecular axis direction is directed to a specific direction in response to an applied electric field because of the dielectric anisotropy of liquid crystal molecules. It is said that the limit of response speed is on the order of milli-seconds, which is too slow for many uses. On the other hand, a simple matrix system of driving is most promising for application to a large-area flat display in view of cost, productivity, etc., in combination. In the simple matrix system, an electrode arrangement wherein scanning electrodes and signal electrodes are arranged in a matrix and for driving, a multiplex driving scheme is adopted wherein an address signal is sequentially, periodically and selectively applied to the scanning electrodes and prescribed data signals are selectively applied in parallel to the signal electrodes in synchronism with the address signal.

When the above-mentioned TN-type liquid crystal is used in a device of such a driving system, a certain electric field is applied to regions where a scanning electrode is selected and signal electrodes are not selected or regions where a scanning electrode is not selected and a signal electrode is selected (which regions are so called "half-selected points"). If the difference between a voltage applied to the selected points and a voltage applied to the half-selected points is sufficiently large, and a voltage threshold level required for allowing liquid crystal molecules to be aligned or oriented perpendicular to an electric field is set to a value therebetween, display devices normally operate. However, in fact, as the number (N) of scanning lines increases, a time (duty ratio) during which an effective electric field is applied to one selected point when a whole image area (corresponding to one frame) is scanned decreases with a ratio of 1/N. Accordingly, the larger the number of scanning lines are, the smaller is the voltage difference of an effective value applied to a selected point and non-selected points when scanning is repeatedly effected. As a result, this leads to unavoidable drawbacks of lowering of image contrast or occurrence of interference or crosstalk. These phenomena are regarded as essentially unavoidable problems appearing when a liquid crystal having no bistability (i.e. liquid crystal molecules are horizontally oriented with respect to the electrode surface as stable state and is vertically oriented with respect to the electrode surface only when an electric field is effectively applied) is driven (i.e. repeatedly scanned) by making use of a time storage effect. To overcome these drawbacks, the voltage averaging method, the two-frequency driving method, the multiple matrix method, etc. has been already proposed. However, any method is not sufficient to overcome the above-mentioned drawbacks. As a result, it is the present state that the development of large image area or high packaging density in respect to display elements is delayed because it is difficult to sufficiently increase the number of scanning lines.

To overcome drawbacks with such prior art liquid crystal devices, the use of liquid crystal devices having bistability has been proposed by Clark and Lagerwall (e.g. Japanese Laid-Open Patent Appln. No. 56-107216, U.S. Pat. No. 4,367,924, etc.). In this instance, as the liquid crystals having bistability, ferroelectric liquid crystals having chiral smectic C-phase (SmC*) or H-phase (SmH*) are generally used. These liquid crystals have bistable states of first and second stable states with respect to an electric field applied thereto. Accordingly, as different from optical modulation devices in which the above-mentioned TN-type liquid crystals are used, the bistable liquid crystal molecules are oriented to first and second optically stable states with respect to one and the other electric field vectors, respectively. Further, this type of liquid crystal has a property (bistability) of assuming either one of the two stable states in response to an applied electric field and retaining the resultant state in the absence of an electric field.

In addition to the above-described characteristic of showing bistability, such a ferroelectric liquid crystal (hereinafter sometimes abbreviated as "FLC") has an excellent property, i.e., a high-speed responsiveness. This is because the spontaneous polarization of the ferroelectric liquid crystal and an applied electric field directly interact with each other to induce transition of orientation states. The resultant response speed is faster than the response speed due to the interaction between dielectric anisotropy and an electric field by 3 to 4 digits.

Thus, a ferroelectric liquid crystal potentially has very excellent characteristics, and by making use of these properties, it is possible to provide essential improvements to many of the above-mentioned problems with the conventional TN-type devices. Particularly, the application to a high-speed optical shutter and a display of a high density and a large picture is expected. For this reason, there has been made extensive research with respect to liquid crystal materials showing ferroelectricity. However, ferroelectric liquid crystal materials developed heretofore cannot be said to satisfy sufficient characteristics required for a liquid crystal device including low-temperature operation characteristic, high-speed responsiveness, etc. Among a response time $\tau$, the magnitude of spontaneous polarization Ps and viscosity $\eta$, the following relationship exists: $\tau = \eta/(Ps \cdot E)$, where E is an applied voltage. Accordingly, a high response speed can be obtained by (a) increasing the spontaneous polarization Ps, (b) lowering the viscosity $\eta$, or (c) increasing the applied voltage E. However, the driving voltage has a certain upper limit in view of driving with IC, etc., and should desirably be as low as possible. Accordingly, it is actually necessary to lower the viscosity or increase the spontaneous polarization.

A ferroelectric chiral smectic liquid crystal having a large spontaneous polarization generally provides a large internal electric field in a cell given by the spontaneous polarization and is liable to pose many constraints on the device construction giving bistability. Further, an excessively large spontaneous polarization is liable to accompany an increase in viscosity, so that remarkable increase in response speed may not be attained as a result.

Further, if it is assumed that the operation temperature of an actual display device is 5°–40° C., the response speed changes by a factor of about 20, so that it actually exceeds the range controllable by driving voltage and frequency.

As described hereinabove, commercialization of a ferroelectric liquid crystal device requires a liquid crystal composition assuming a chiral smectic phase which has not only a large spontaneous polarization but also a low viscosity, a high-speed responsiveness and a small temperature-dependence of response speed.

SUMMARY OF THE INVENTION

An object of the present invention is to provide a mesomorphic compound, a liquid crystal composition, particularly a chiral smectic liquid crystal composition, containing the mesomorphic compound for providing a practical ferroelectric liquid crystal device, a liquid crystal device using the liquid crystal composition and having a high response speed and a smaller temperature-dependence of the response speed, a display apparatus using the device, and a display method using the composition and device.

According to the present invention, there is provided a mesomorphic compound represented by the following formula (I):

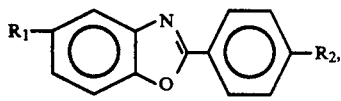
(I)

wherein $R_1$ and $R_2$ respectively denote an alkyl group or alkoxy group each having 4–16 carbon atoms optionally substituted, halogen, —CN or —CF$_3$.

According to the present invention, there is further provided a liquid crystal composition containing at least one species of the mesomorphic compound as described above.

The present invention provides a liquid crystal device comprising a pair of electrode plates and the liquid crystal composition described above disposed between the electrode plates.

The present invention further provides a display apparatus comprising the liquid crystal device, and voltage application means for driving the liquid crystal device.

The present invention still further provides a display method using the liquid crystal composition or the liquid crystal device described above and switching the alignment direction of liquid crystal molecules by applying voltages to the liquid crystal composition to effect display.

Heretofore, mesomorphic compounds containing a 2-phenylbenzoxazole skeleton have been shown in A. I. Pavluchenko, et at., "Mol. Cryst. Liq. Cryst.", 37 35–46 (1976). However, the 2-phenylbenzoxazole derivatives developed as nematic liquid crystals and disclosed in the above reference only include a mesomorphic compound corresponding to one represented by the formula (I) wherein $R_1$ is methyl or methoxy.

We have accomplished the present invention based on a discovery of the compounds of the formula (I) wherein $R_1$ is an alkyl or alkoxy group having 4–16 carbon atoms, as a suitable class of mesomorphic compounds showing chiral smectic C phase.

More specifically, we found that the 2-phenylbenzoxazole derivative represented by the formula (I) according to the present invention had a wider temperature range of a smectic C phase compared with the 2-phenylbenzoxazole derivative disclosed in the above document. Further, we found that a liquid crystal composition containing the 2-phenylbenzoxazole derivative of the formula (I) according to the present invention showed a wider temperature range of chiral smectic C phase compared with that of a liquid crystal composition containing the 2-phenylbenzoxazole derivative of the above reference. We also found that a liquid crystal device using a ferroelectric chiral smectic liquid crystal composition containing the above phenylbenzoxazole derivative of the invention showed an improved low-temperature operation characteristic and a decreased temperature-dependence of response speed. The above results are demonstrated in Examples 3, 6 and 7 and Comparative Example 1 appearing hereinafter.

These and other objects, features and advantages of the present invention will become more apparent upon a consideration of the following description of the preferred embodiments of the present invention taken in conjunction with the accompanying drawings.

DETAILED DESCRIPTION OF THE INVENTION

Figure 1:
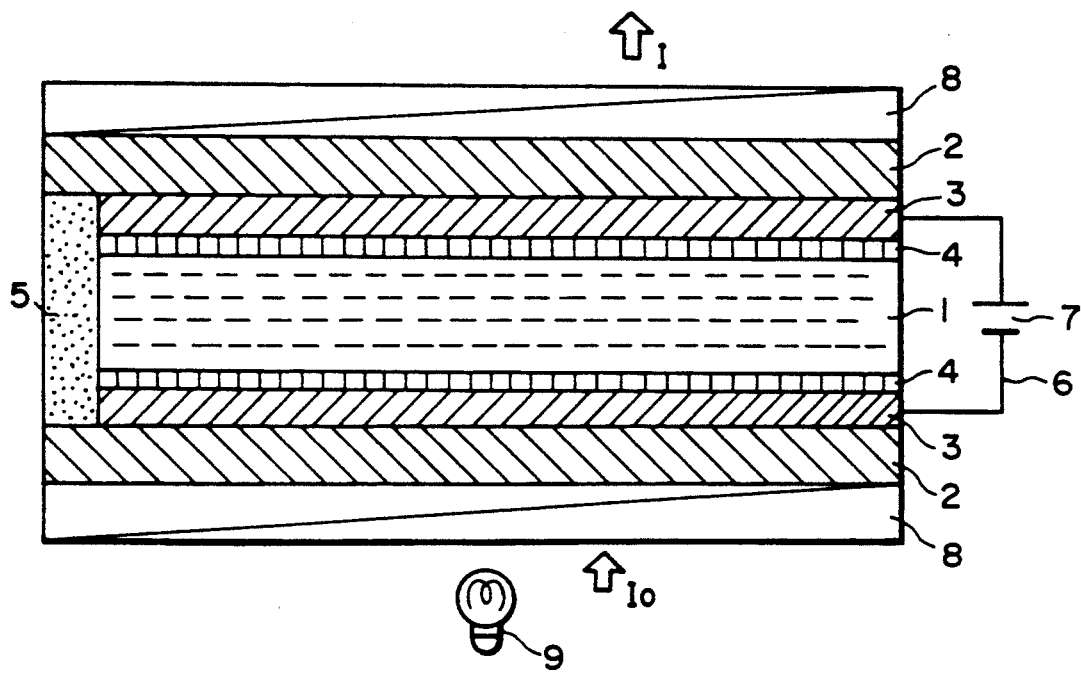
FIG. 1 is a schematic sectional view of a liquid crystal display device using a liquid crystal composition assuming a chiral smectic phase.

In the formula (I) as described above, preferred examples of $R_1$ and $R_2$ each may preferably include the following groups (i) to (v):

(i) an n-alkyl group or n-alkoxy group each having 4–16 carbon atoms, particularly 4–12 carbon atoms;

(ii)

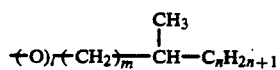

wherein l is 0 or 1, m is an integer of 0–6 and n is an integer of 1–8 (optically active or inactive);

(iii)

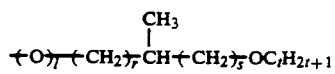

wherein l is 0 or 1, r is an integer of 0-6, s is 0 or 1, and t is an integer of 1-12 (optically active or inactive);

(iv)

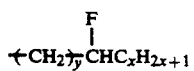

wherein y is 0 or 1 and x is an integer of 1-14; and (v) fluorine (F), bromine (Br), chlorine (Cl), cyano (—CN) or trifluoromethyl (—CF$_3$), particularly F or —CF$_3$.

The mesomorphic compounds represented by the general formula (I) may be synthesized through the following reaction schemes.

ble to form a group of R$_1$'O— or R$_2$'O— through the following scheme A or B.

SCHEME A (1) Hydroxyl group combined with a benzene ring is modified with addition of a protective group into a non-reactive or less reactive group such as —OCH$_3$,

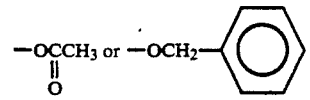

capable of elimination reaction.

(2) Ring closure ② or ③ is effected.

(3) The protective group is eliminated to provide hydroxyl group and modified into the R$_1$'O— or R$_2$'O— structure.

SCHEME B (1) Nitro group (—NO$_2$) or acetyl group (CH$_3$CO—)

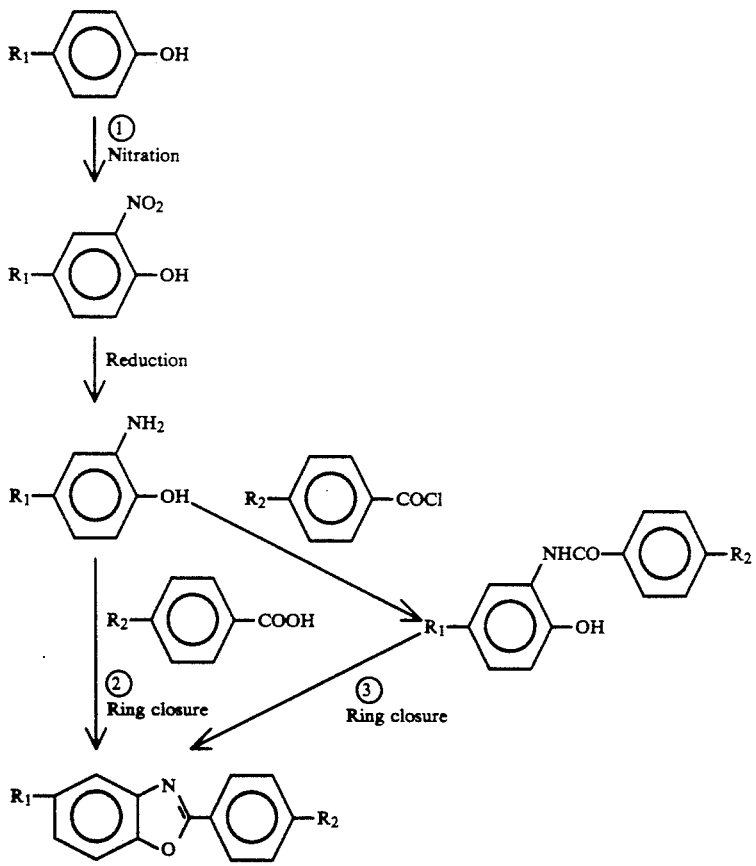

Nitration ① of phenols can be conducted by using methods shown in L. Gattermann, "Die Praxis des Organischem Chemikers", pp. 214, R. Adams et al. "J. Am. Chem. Soc.", 63, 196 (1941), etc. Ring closure ② and ③ wherein o-aminophenols change into compounds having benzoxazole rings can be conducted by using methods shown in D. W. Hein et al., "J. Am. Chem. Soc.", 79, 427 (1957), Y. Kanaoka et al. "Chem. Pharm. Bull.", 18, 587 (1970), etc. In case where R$_1$ or R$_2$ is an alkoxy group R$_1$'O— or R$_2$'O—, it is also possicapable of modifying into hydroxyl group is combined with a benzene ring.

(2) Ring closure ② or ③ is effected.

(3) Nitro group or acetyl group is modified into hydroxyl group and further modified into the R$_1$'O— or R$_2$'O— structure.

Specific examples of the mesomorphic compounds represented by the above-mentioned general formula (I) may include those shown by the following structural formulas.

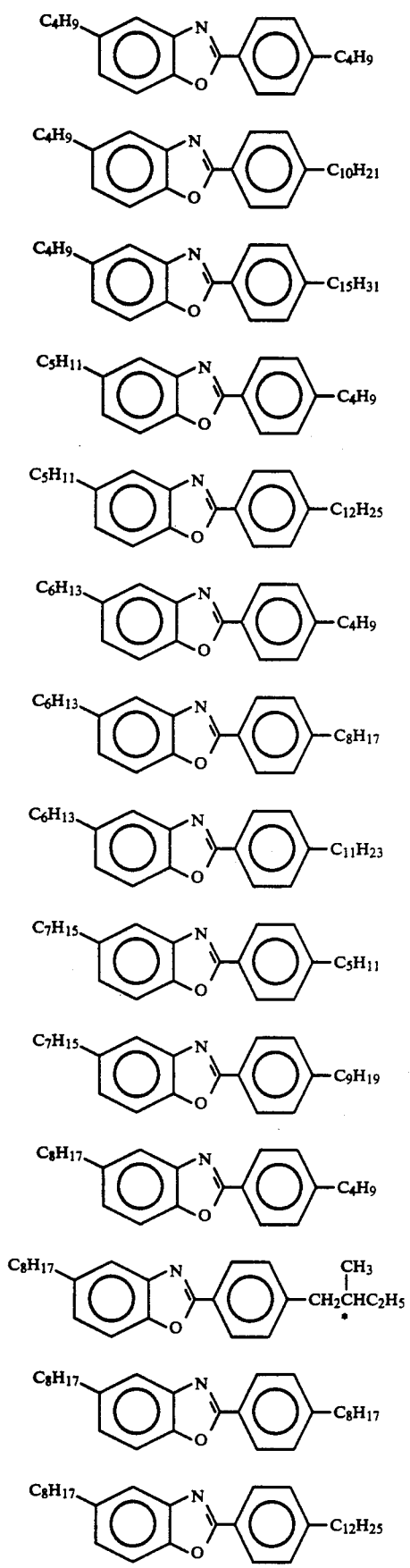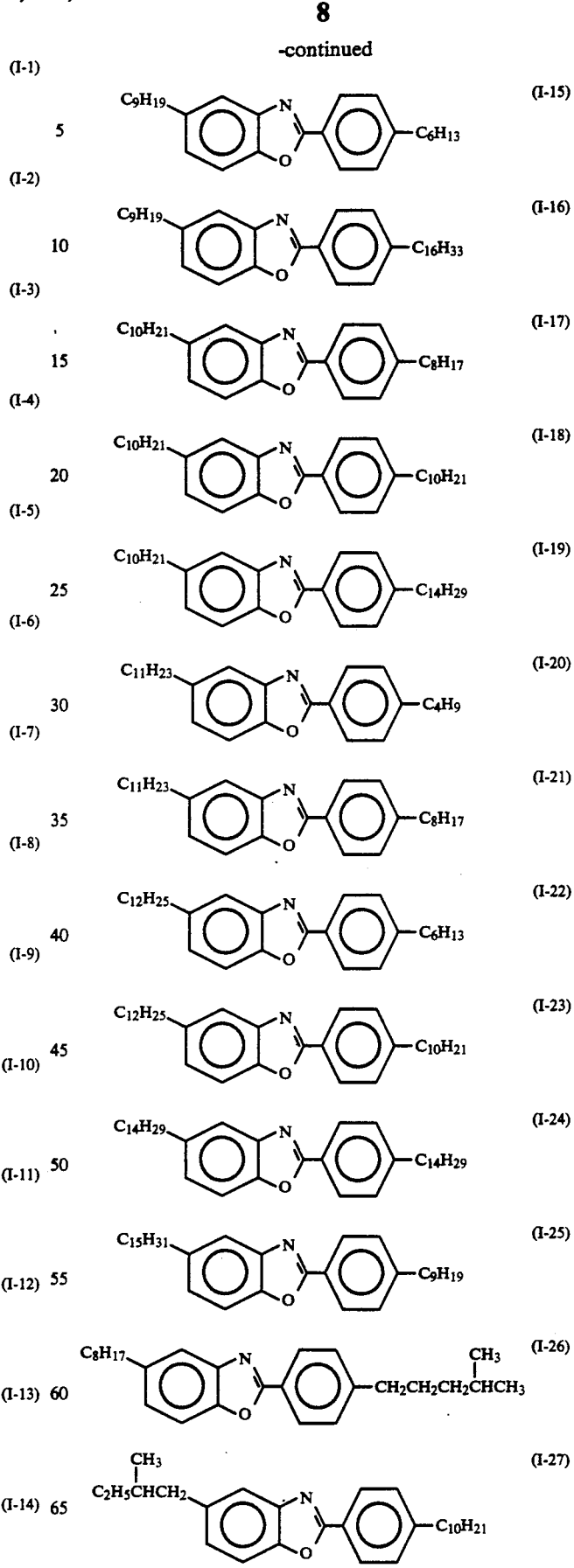

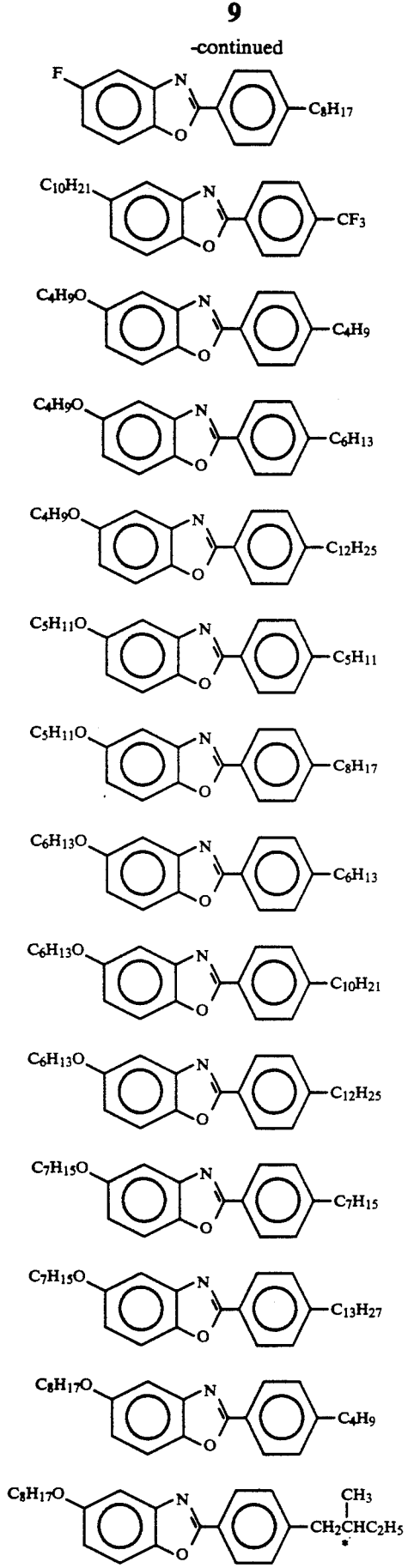
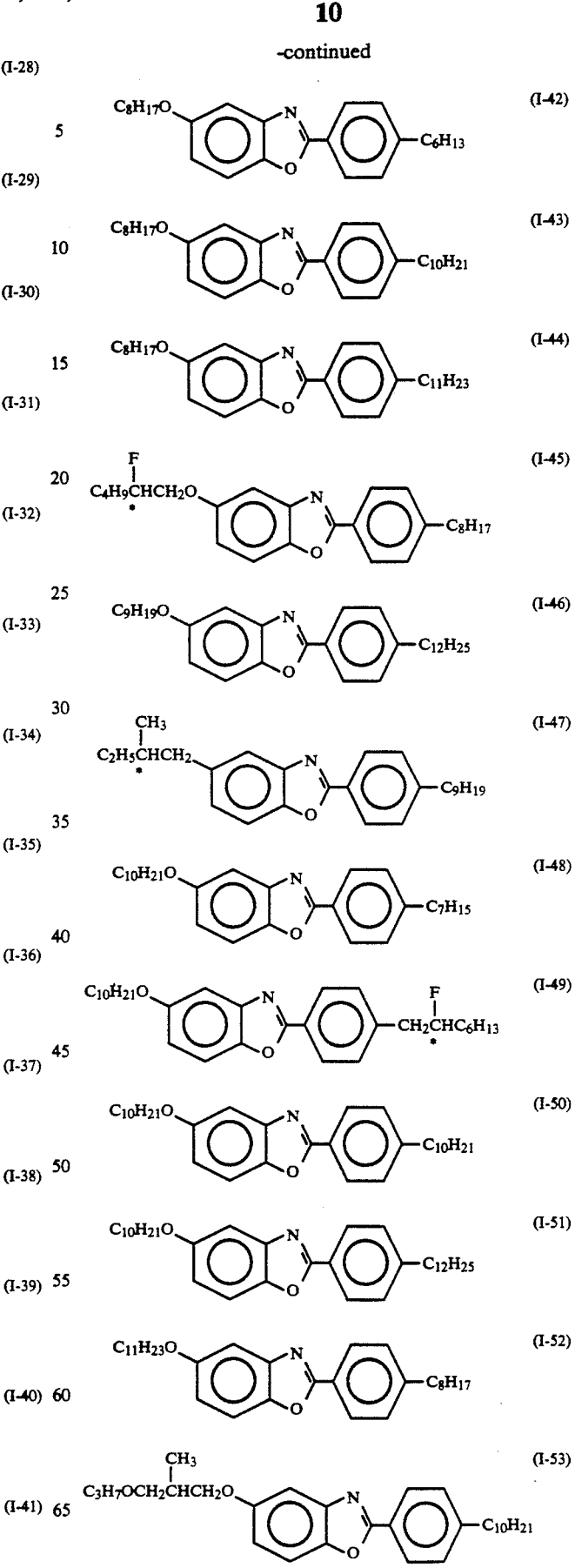

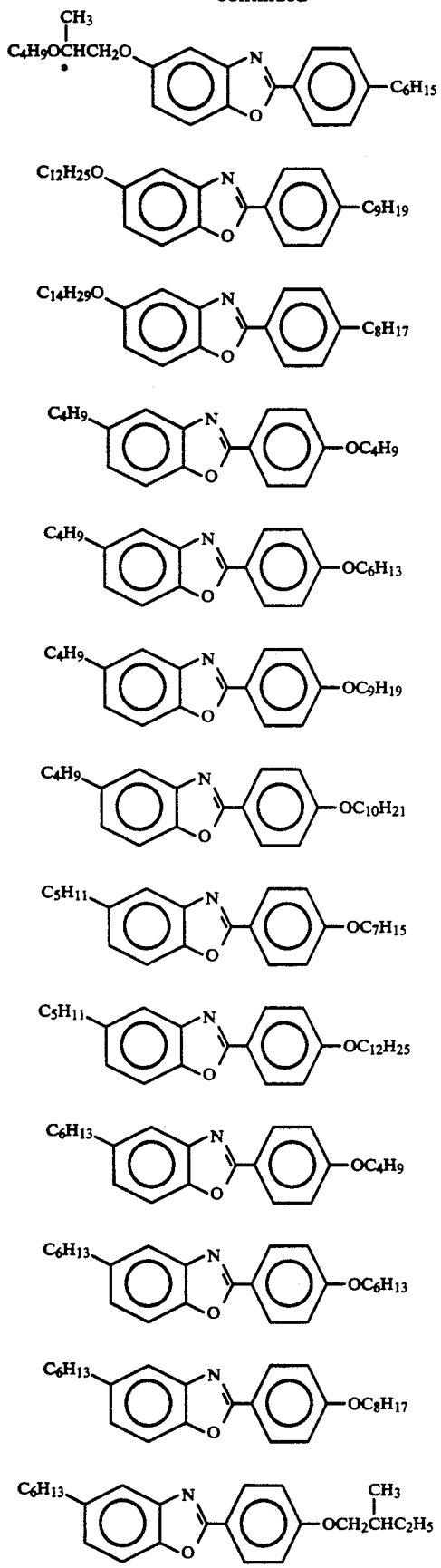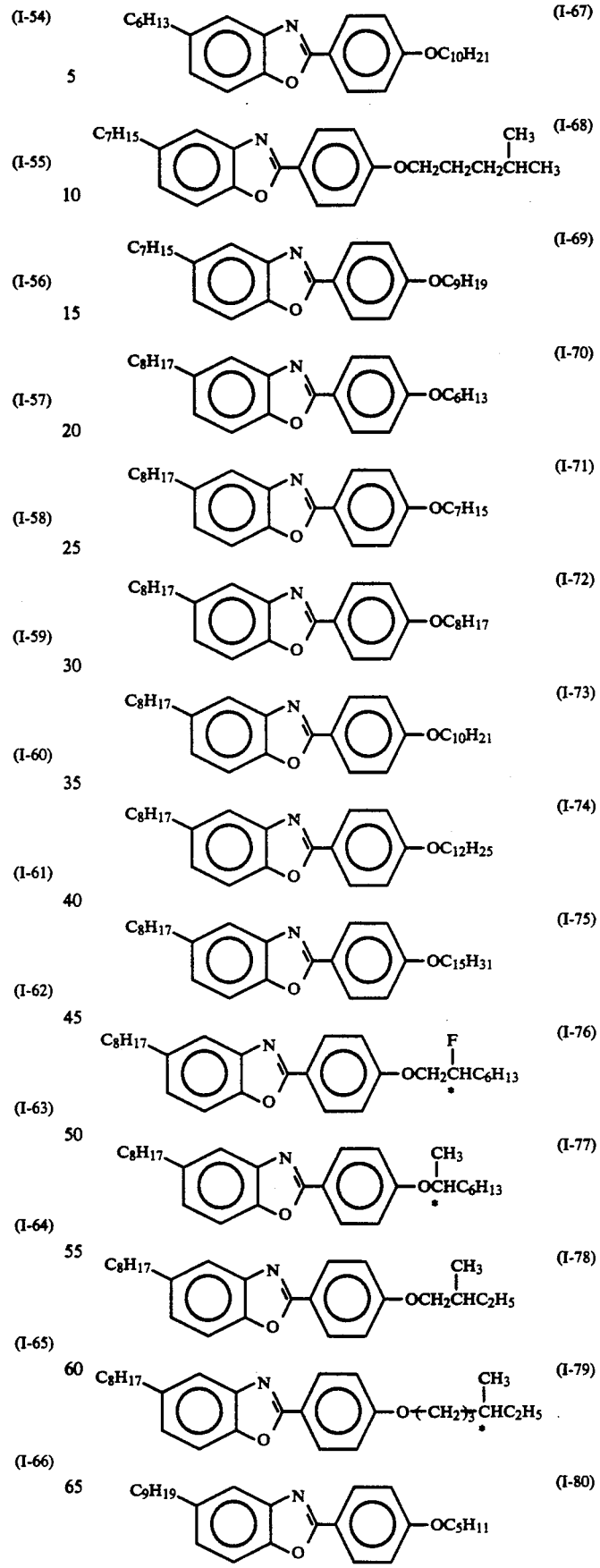

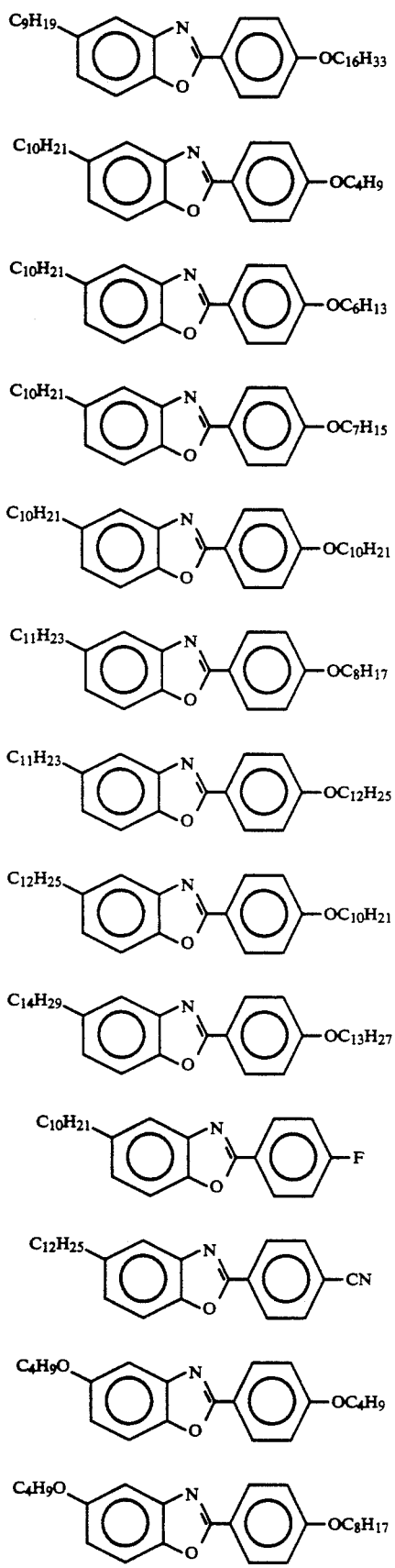
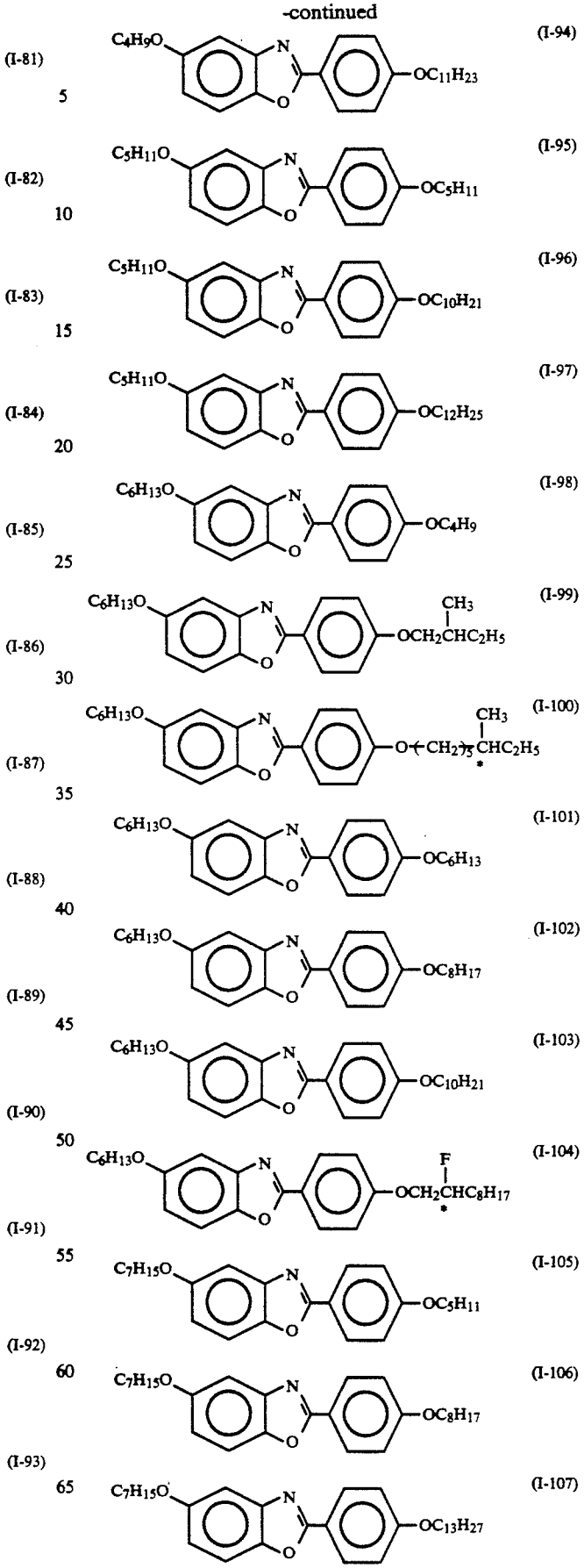

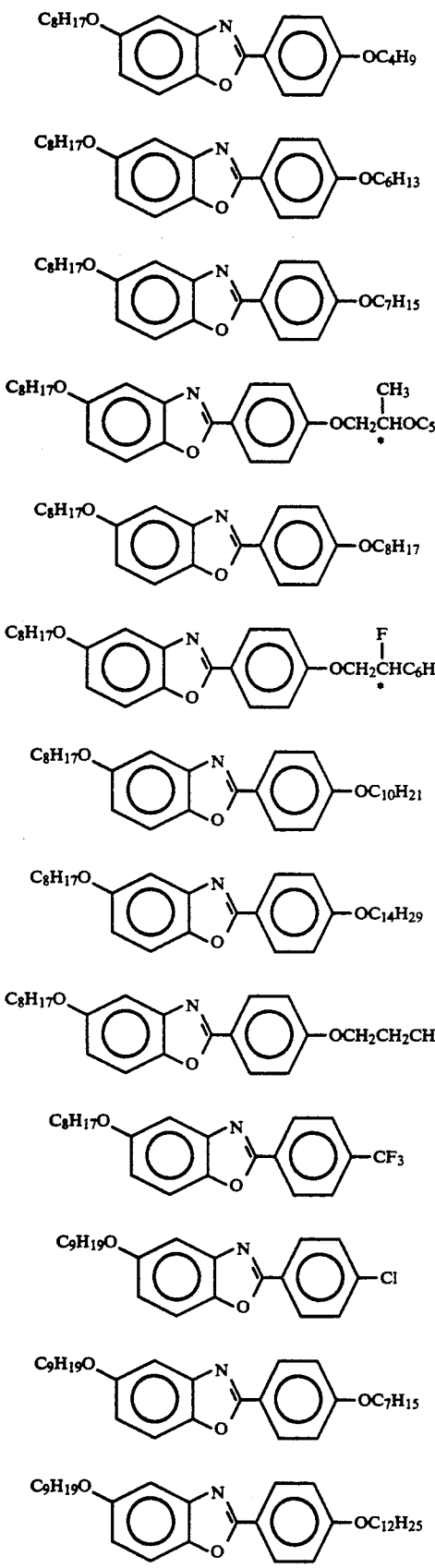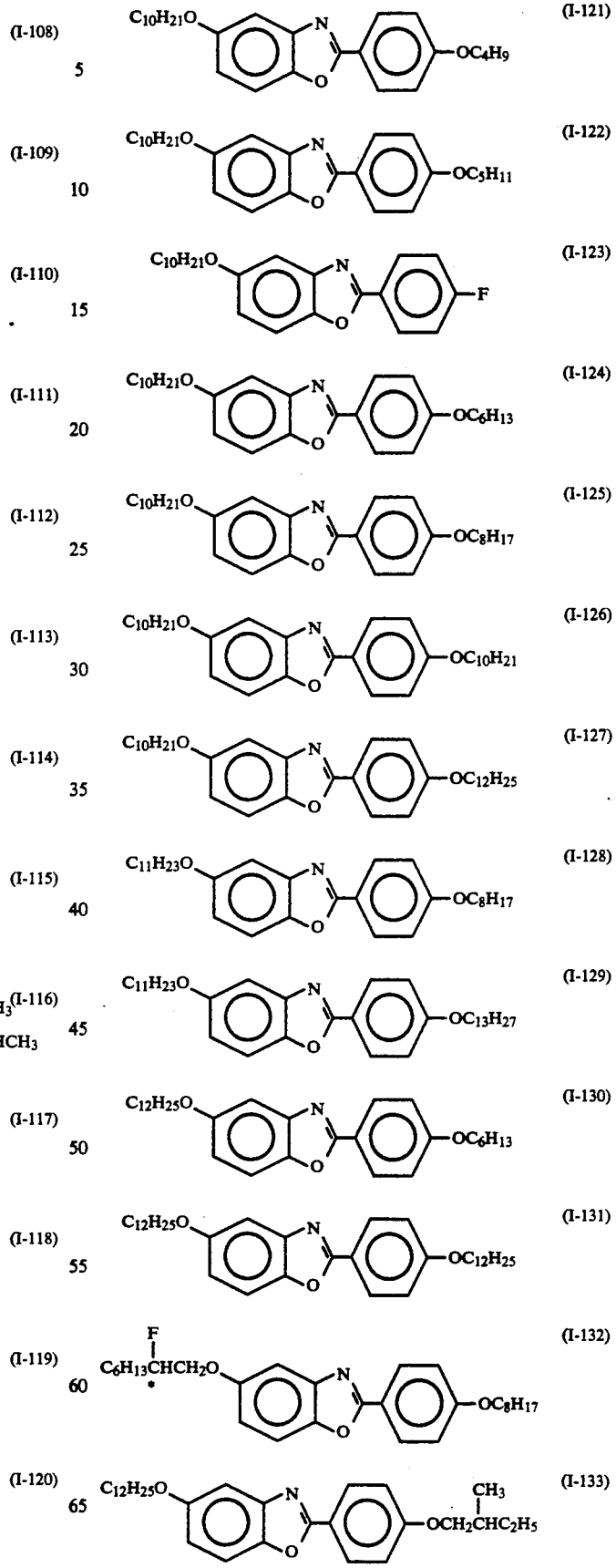

-continued

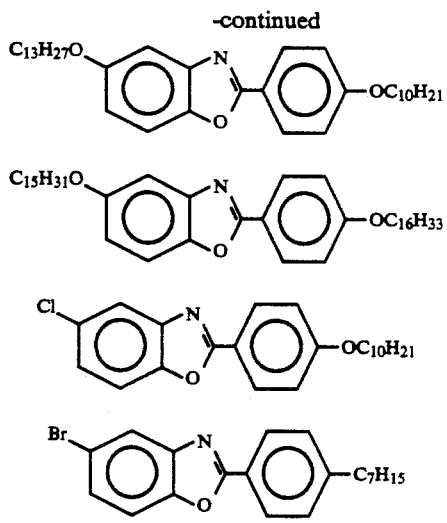

(I-134)
(I-135)
(I-136)
(I-137)
(I-138)
(I-139)

-continued

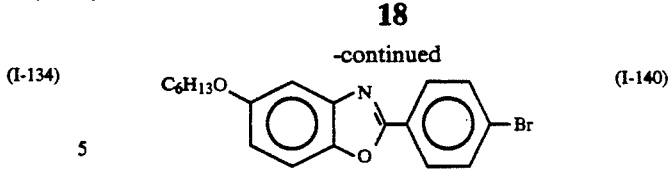

(I-140)

The liquid crystal composition according to the present invention may be obtained by mixing at least one species of the compound represented by the formula (I) and another mesomorphic compound in appropriate proportions. The liquid crystal composition according to the present invention may preferably be formulated as a liquid crystal composition capable of utilizing ferroelectricity, particularly a liquid crystal composition showing a chiral smectic phase.

Specific examples of another mesomorphic compound as described above may include those denoted by the following formulas (III) to (XI).

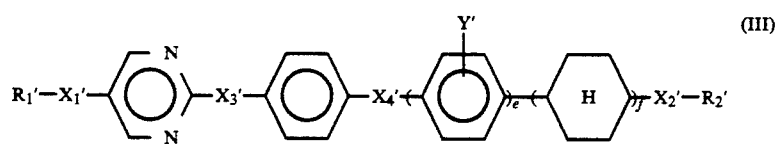

(III)

wherein e denotes 0 or 1 and f denotes 0 or 1 with proviso that e+f=0 or 1; Y' denotes H, halogen, $CH_3$ or $CF_3$; $X_1'$ and $X_2'$ respectively denote a single bond,

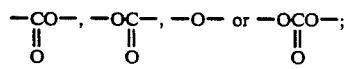

and $X_3'$ and $X_4'$ respectively denote a single bond,

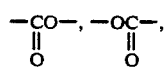

In the formula (III), preferred compounds thereof may include those represented by the following formulas (IIIa) to (IIId):

(IIIa)

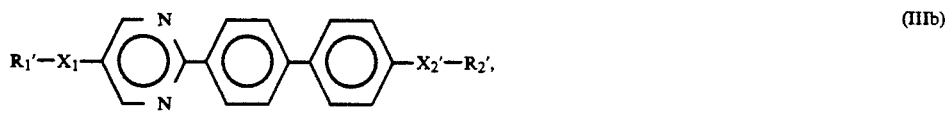

(IIIb)

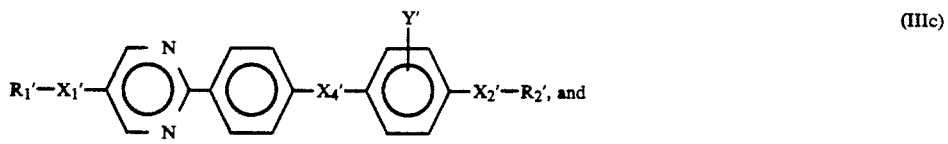

(IIIc)

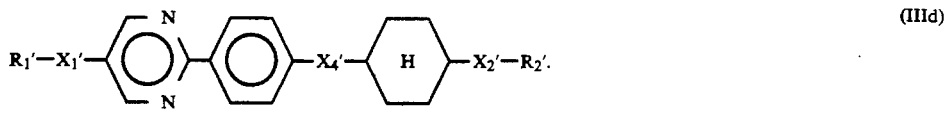

(IIId)

-continued

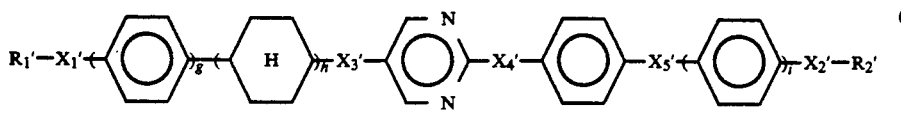
(IV)

wherein g and h respectively denote 0 or 1 with proviso that g+h=1; i denotes 0 or 1; $X_1'$ and $X_2'$ respectively denote a single bond,

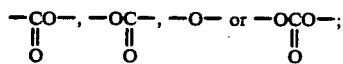

and $X_3'$, $X_4'$ and $X_5'$ respectively denote a single bond,

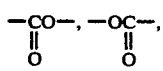

—CH$_2$O— or —OCH$_2$—.

In the formula (IV), preferred compounds thereof may include those represented by the following formulas (IVa) to (IVc):

wherein j denotes 0 or 1; $Y_1'$, $Y_2'$ and $Y_3'$ respectively denote H, halogen, CH$_3$ or CF$_3$; $X_1'$ and $X_2'$ respectively denote a single bond,

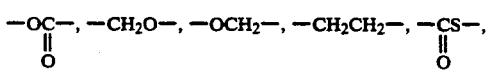

and $X_3'$ and $X_4'$ respectively denote a single bond, $$-\underset{O}{\overset{}{\text{OC}}}-, -CH_2O-, -OCH_2-, -CH_2CH_2-, -\underset{}{\overset{}{\text{CS}}}-,$$

$$-\underset{O}{\overset{}{\text{SC}}}-, -(CH_2)_2CS-, -(CH_2)_2CO-, -CH=CH-\underset{O}{\overset{}{\text{CO}}}-$$

or —O—.

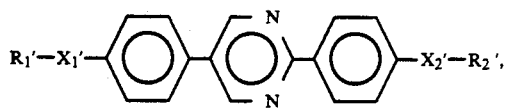
(IVa)

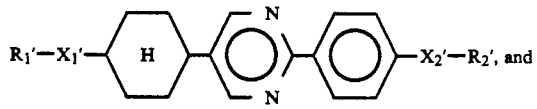
(IVb)

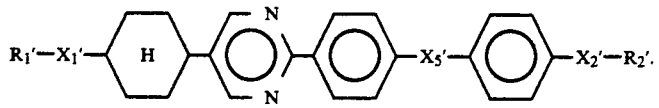
(IVc)

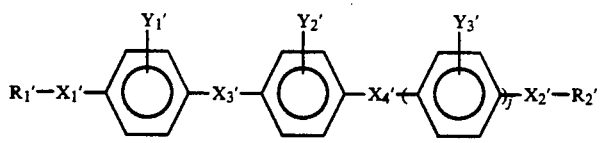
(V)

In the formula (V), preferred compounds thereof may include those represented by the following formulas (Va) and (Vb):

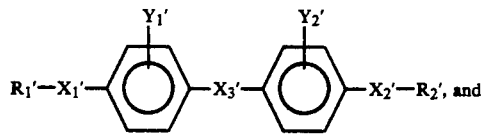
(Va)

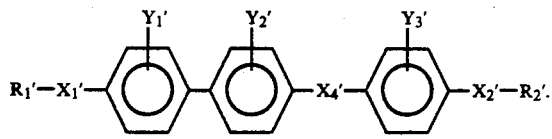
(Vb)

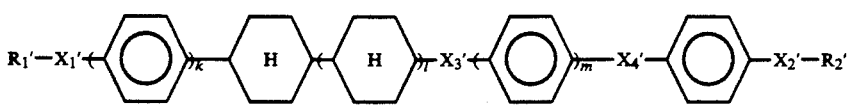
(VI)

wherein k, l and m respectively denote 0 or 1 with proviso that k+l+m=0, 1 or 2; $X_1'$ and $X_2'$ respectively denote a single bond,

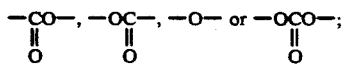

and $X_3'$ and $X_4'$ respectively denote a single bond,

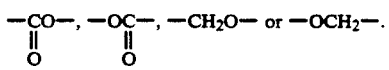

In the formula (VI), preferred compounds thereof may include those represented by the following formulas (VIa) to (VIf):

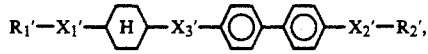
(VIa)

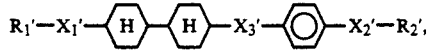
(VIb)

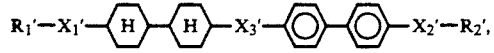
(VIc)

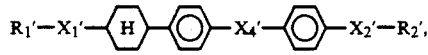
(VId)

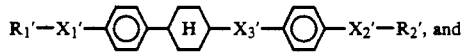
(VIe)

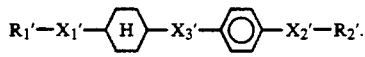
(VIf)

Herein, $R_1'$ and $R_2'$ respectively denote a linear or branched alkyl group having 1-18 carbon atoms capable of including one or two or more non-neighboring methylene groups which can be replaced with —CH halogen- and capable of further including one or two or more non-neighboring methylene groups other than those directly connected to $X_1'$ or $X_2'$ which can be replaced with at least one species of —O—,

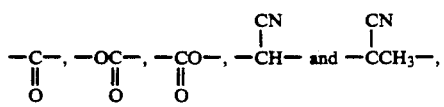

with proviso that $R_1'$ and $R_2'$ respectively do not connect to a ring structure by a single bond when $R_1'$ and $R_2'$ respectively denote a halogenated alkyl group containing one methylene group replaced with —CH halogen-.

Further, preferred examples of $R_1'$ and $R_2'$ may respectively include those represented by the following groups (i) to (vii):

i) a linear alkyl group having 1-15 carbon atoms;
ii)

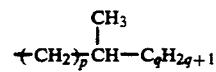

wherein p denotes an integer of 0-5 and q denotes an integer of 1-11 (optically active or inactive);
iii)

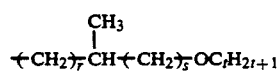

wherein r denotes an integer of 0-6, s denotes 0 or 1, and t denotes an integer of 1-14 (optically active or inactive);
iv)

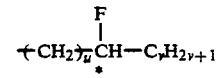

wherein u denotes 0 or 1 and v denotes an integer of 1-16;
v)

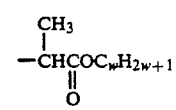

wherein w denotes an integer of 1-15 (optically active or inactive);
vi)

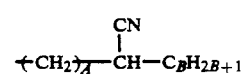

wherein A denotes an integer of 0-2 and B denotes an integer of 1-15 (optically active or inactive); and
vii)

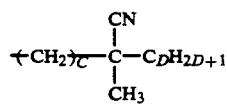

wherein C denotes an integer of 0-2 and D denotes an integer of 1-15 (optically active or inactive).

In the above-mentioned formula (III), more preferred compounds thereof may include those represented by the formulas (IIIaa) to (IIIdc):

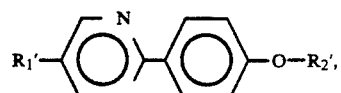
(IIIaa)

-continued

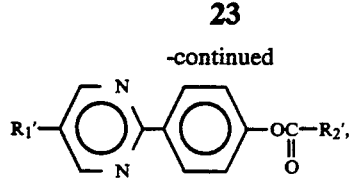 (IIIab)

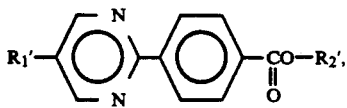 (IIIac)

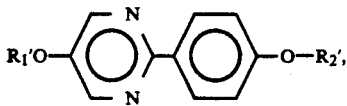 (IIIad)

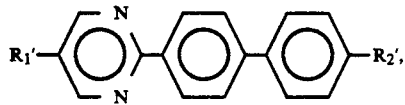 (IIIba)

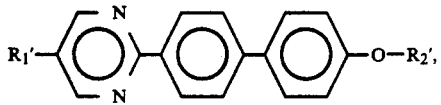 (IIIbb)

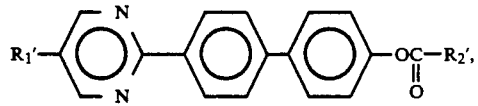 (IIIbc)

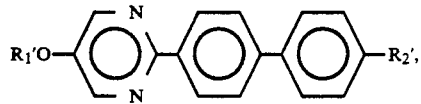 (IIIbd)

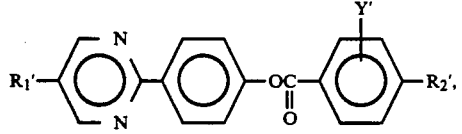 (IIIca)

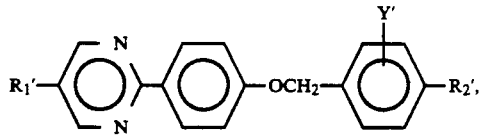 (IIIcb)

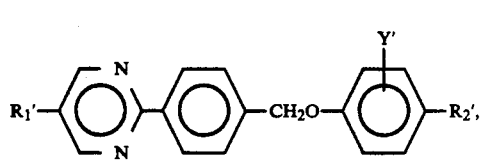 (IIIcc)

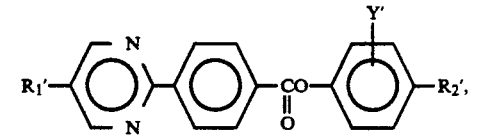 (IIIcd)

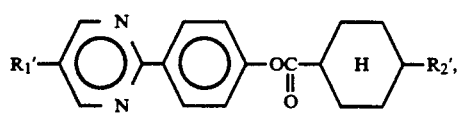 (IIIda)

-continued

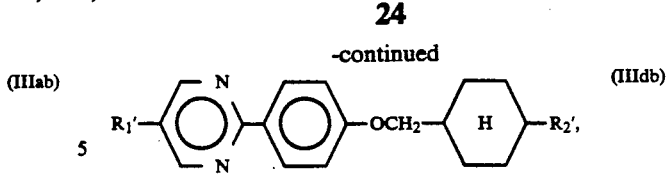 (IIIdb)

and

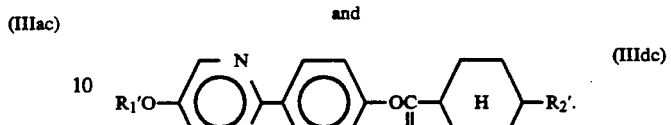 (IIIdc)

In the above-mentioned formula (IV), more preferred compounds thereof may include those represented by the formulas (IVaa) to (IVcd):

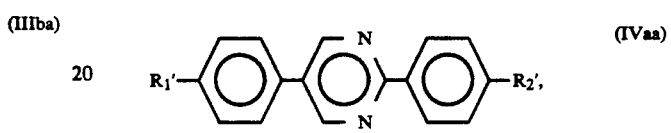 (IVaa)

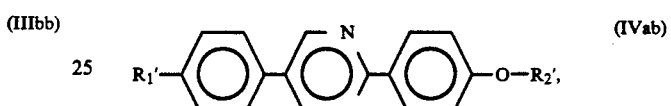 (IVab)

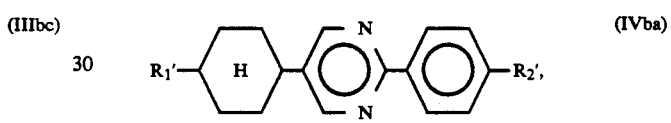 (IVba)

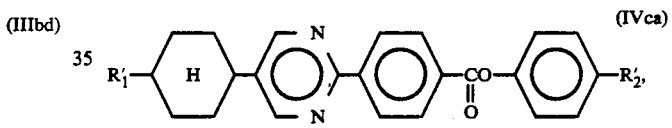 (IVca)

and

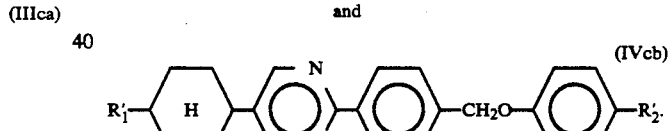 (IVcb)

In the above-mentioned formula (V), more preferred compounds thereof may include those represented by the formulas (Vaa) to (Vbf):

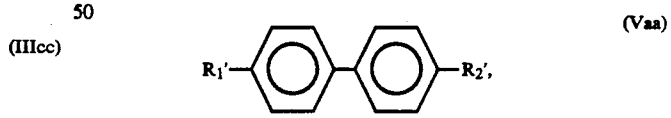 (Vaa)

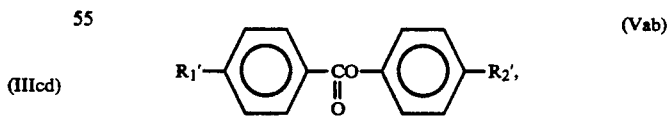 (Vab)

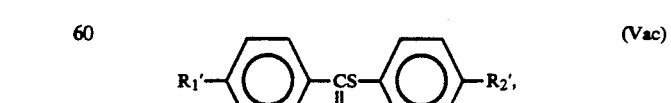 (Vac)

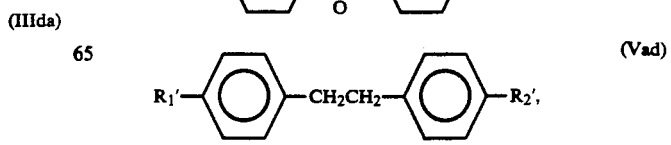 (Vad)

-continued

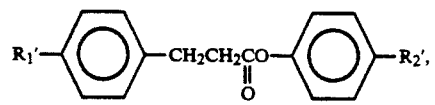 (Vae)

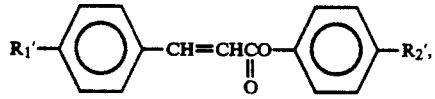 (Vaf)

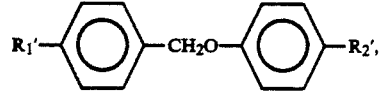 (Vag)

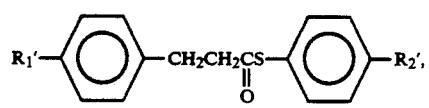 (Vah)

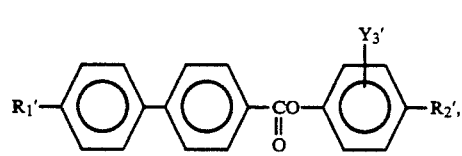 (Vba)

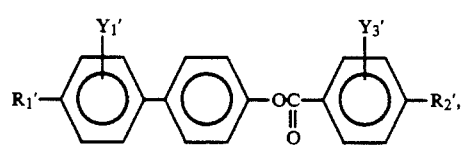 (Vbb)

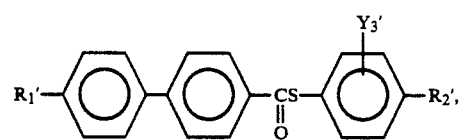 (Vbc)

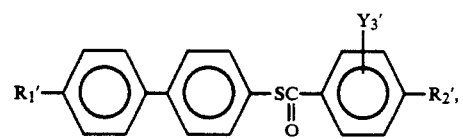 (Vbd)

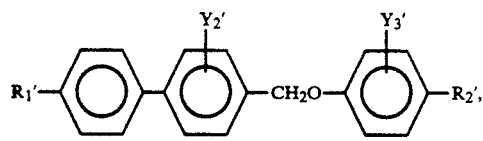 (Vbe)

and

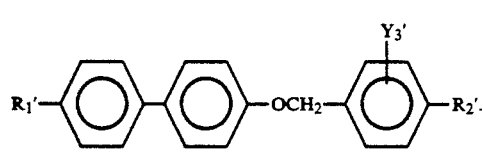 (Vbf)

In the above-mentioned formula (VI), more preferred compounds thereof may include those represented by the formulas (VIaa) to (VIfa):

 (VIaa)

 (VIab)

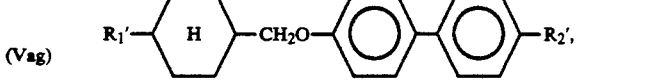 (VIba)

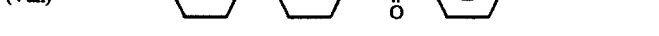 (VIbb)

 (VIda)

 (VIea)

 (VIfa)

 (VII)

wherein E denotes 0 or 1; $X_1'$ and $X_2'$ respectively denote a single bond,

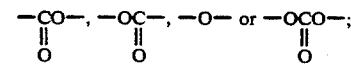

and $X_3'$ denotes a single bond,

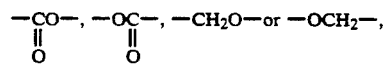

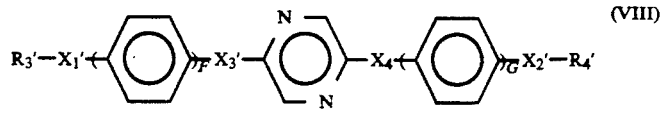 (VIII)

wherein F and G respectively denote 0 or 1; $X_1'$ and $X_2'$ respectively denote a single bond,

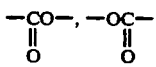

or —O—; and $X_3'$ and $X_4'$ respectively denote a single bond,

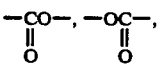

—CH$_2$O— or —OCH$_2$—.

In the above formula (VII), preferred compounds thereof may include those represented by the following formulas (VIIa) and (VIIb):

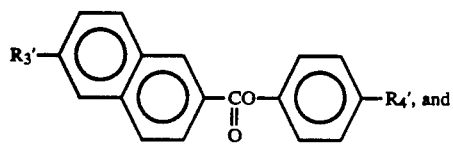

(VIIa)

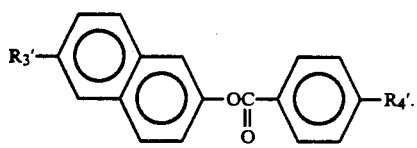

(VIIb)

In the above formula (VIII), preferred compounds thereof may include those represented by the following formulas (VIIIa) and (VIIIb).

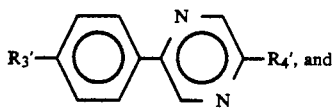

(VIIIa)

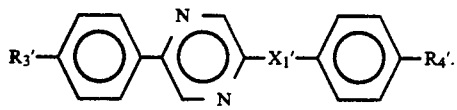

(VIIIb)

More preferred compounds of the formula (VIII) may include those represented by the formulas (VIIIaa) to (VIIIbb):

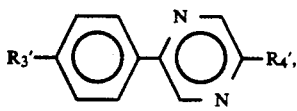

(VIIIaa)

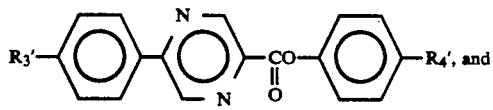

(VIIIba)

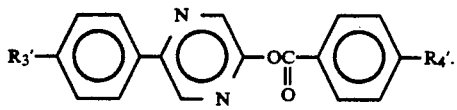

(VIIIbb)

Herein, $R_3'$ and $R_4'$ respectively denote a linear or branched alkyl group having 1-18 carbon atoms capable of including one or two or more non-neighboring methylene groups which can be replaced with —CH halogen- and capable of further including one or two or more non-neighboring methylene groups other than those directly connected to $X_1'$ or $X_2'$ which can be replaced with at least one species of —O—,

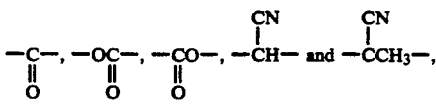

with proviso that $R_3'$ and $R_4'$ respectively do not connect to a ring structure by a single bond when $R_3'$ and $R_4'$ respectively denote a halogenated alkyl group containing one methylene group replaced with —CH halogen-.

Further, preferred examples of $R_3'$ and $R_4'$ may respectively include those represented by the following groups (i) to (vii):

i) a linear alkyl group having 1-15 carbon atoms;

ii)

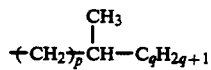

wherein p denotes an integer of 0-5 and q denotes an integer of 1-11 (optically active or inactive);

iii)

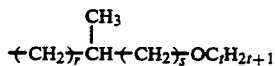

wherein r denotes an integer of 0-6, s denotes 0 or 1, and t denotes an integer of 1-14 (optically active or inactive);

iv)

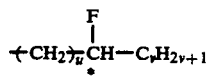

wherein u denotes an integer of 0 or 1 and v denotes an integer of 1-16;

v)

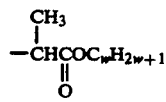

wherein w denotes an integer of 1-15 (optically active or inactive);

vi)

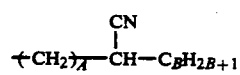

wherein A denotes an integer of 0-2 and B denotes an integer of 1-15 (optically active or inactive); and vii)

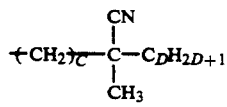

wherein C denotes an integer of 0–2 and D denotes an integer of 1–15 (optically active or inactive).

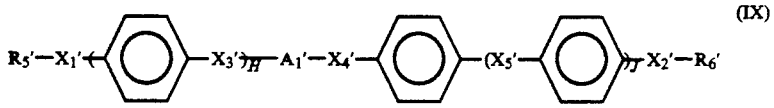

wherein H and J respectively denote 0 or 1 with proviso that H+J=0 or 1; $X_1'$ and $X_2'$ respectively denote a single bond,

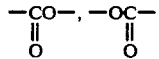

or —O—; $A_1'$ denotes

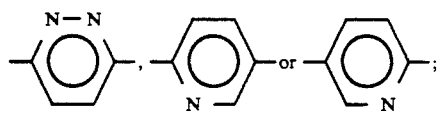

and $X_3'$ and $X_4'$ respectively denote a single bond,

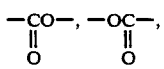

—CH$_2$O— or —OCH$_2$—.

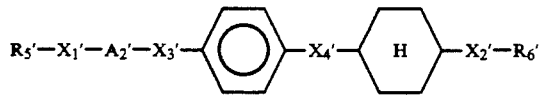

wherein $X_1'$ and $X_2'$ respectively denote a single bond,

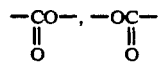

or —O—; $A_2'$ denotes

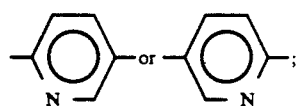

and $X_3'$ and $X_4'$ respectively denote a single bond,

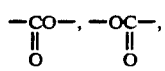

—CH$_2$O— or —OCH$_2$—.

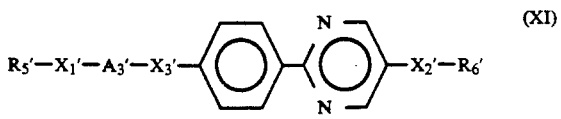

wherein $X_1'$ and $X_2'$ respectively denote a single bond,

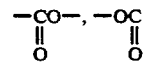

or —O—; $A_3'$ denotes

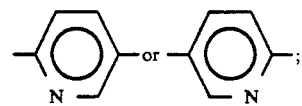

and $X_3'$ respectively denotes a single bond,

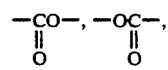

—CH$_2$O— or —OCH$_2$—.

In the above formula (IX), preferred compounds thereof may include those represented by the following formulas (IXa) to (IXc):

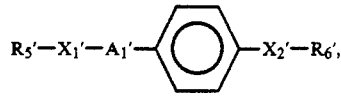

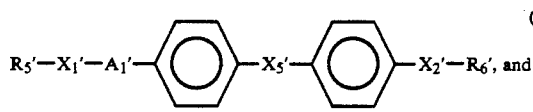

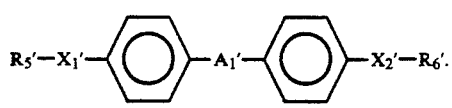

In the above formula (X), preferred compounds thereof may include those represented by the following formulas (Xa) and (Xb):

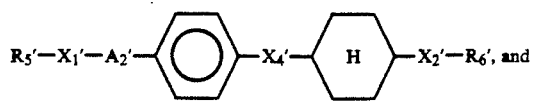

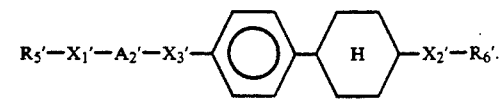

In the above-mentioned formula (IX), more preferred compounds thereof may include those represented by the formulas (IXaa) to (IXcc):

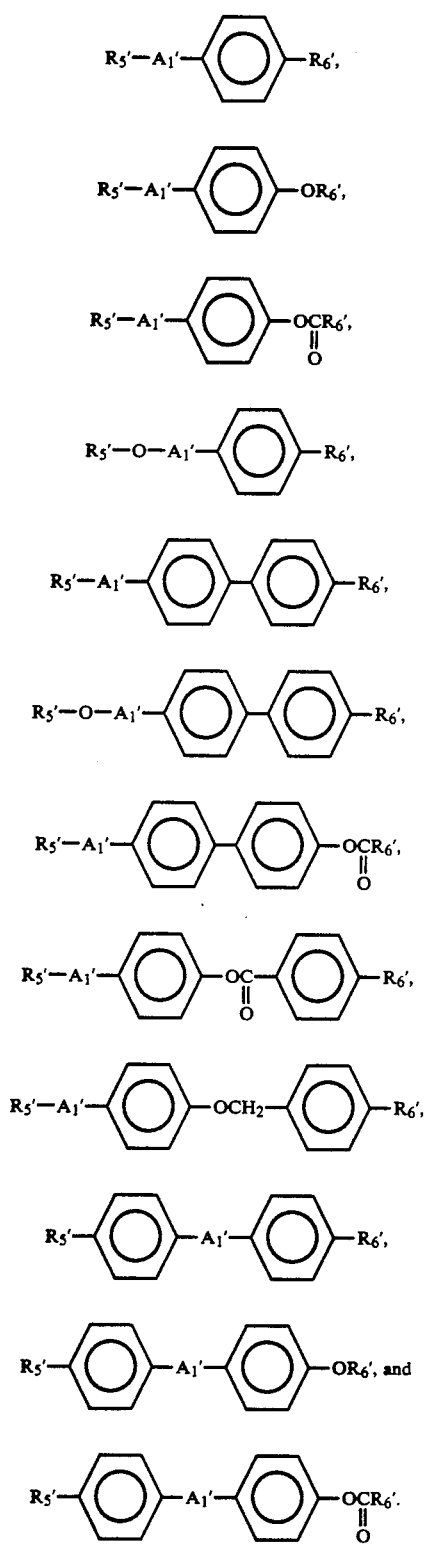

In the above-mentioned formula (X), more preferred compounds thereof may include those represented by the formulas (Xaa) to (Xbb):

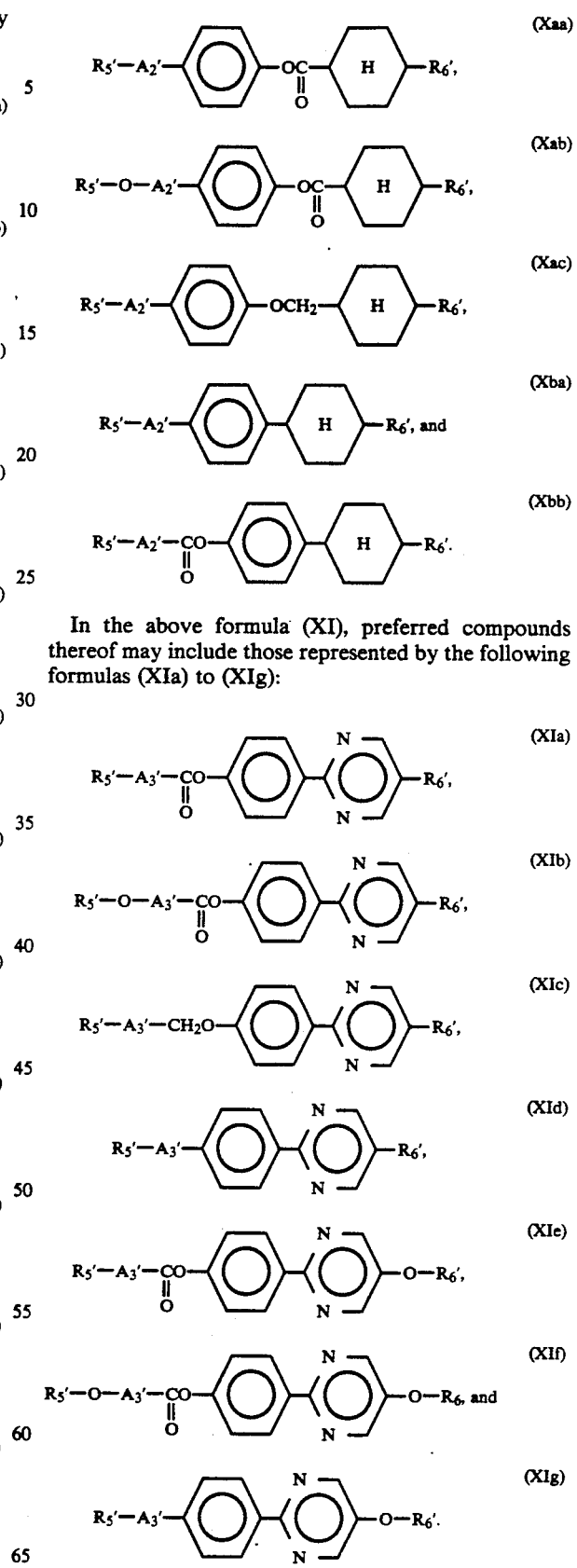

In the above formula (XI), preferred compounds thereof may include those represented by the following formulas (XIa) to (XIg):

Herein, $R_5'$ and $R_6'$ respectively denote a linear or branched alkyl group having 1–18 carbon atoms capable of including one or two or more non-neighboring methylene groups other than those directly connected to $X_1'$ or $X_2'$ which can be replaced with at least one species of —O—,

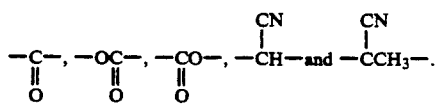

Further, preferred examples of $R_5'$ and $R_6'$ may respectively include those represented by the following groups (i) to (vi):

i) a linear alkyl group having 1-15 carbon atoms;

ii)

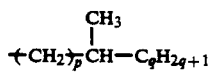

wherein p denotes an integer of 0-5 and g denotes an integer of 1-11 (optically active or inactive);

iii)

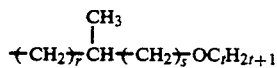

wherein r denotes an integer of 0-6, s denotes 0 or 1, and t denotes an integer of 1-14 (optically active or inactive);

iv)

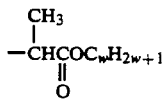

wherein w denotes an integer of 1-15 (optically active or inactive);

v)

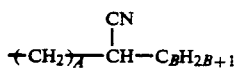

wherein A denotes an integer of 0-2 and B denotes an integer of 1-15 (optically active or inactive); and vi)

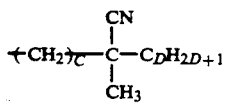

wherein C denotes an integer of 0-2 and D denotes an integer of 1-15 (optically active or inactive).

In formulating the liquid crystal composition according to the present invention, the liquid crystal composition may desirably contain 1-80 wt. %, preferably 1-60 wt. %, more preferably 1-40 wt. % of a mesomorphic compound represented by the formula (I).

Further, when two or more species of the compounds represented by the formula (I) are used, the liquid crystal composition may desirably contain 1-80 wt. %, preferably 1-60 wt. %, more preferably 1-40 wt. %, of the two or more species of the compounds represented by the formula (I).

The liquid crystal device according to the present invention may preferably be prepared by heating the liquid crystal composition assuming a chiral smectic phase prepared as described above into an isotropic liquid under vacuum, filling a blank cell comprising a pair of oppositely spaced electrode plates with the composition, gradually cooling the cell to form a liquid crystal layer and restoring the normal pressure.

FIG. 1 is a schematic sectional view of an embodiment of the liquid crystal device utilizing ferroelectricity prepared as described above for explanation of the structure thereof.

Referring to FIG. 1, the liquid crystal device includes a liquid crystal layer 1 assuming a chiral smectic phase disposed between a pair of glass substrates 2 each having thereon a transparent electrode 3 and an insulating alignment control layer 4. Lead wires 6 are connected to the electrodes so as to apply a driving voltage to the liquid crystal layer 1 from a power supply 7. Outside the substrates 2, a pair of polarizers 8 are disposed so as to modulate incident light $I_0$ from a light source 9 in cooperation with the liquid crystal 1 to provide modulated light I.

Each of two glass substrates 2 is coated with a transparent electrode 3 comprising a film of $In_2O_3$, $SbnO_2$ or ITO (indium-tin-oxide) to form an electrode plate. Further thereon, an insulating alignment control layer 4 is formed by rubbing a film of a polymer such as polyimide with gauze or acetate fiber-planted cloth so as to align the liquid crystal molecules in the rubbing direction Further, it is also possible to compose the alignment control layer of two layers, e.g., by first forming an insulating layer of an inorganic material, such as silicon nitride, silicon nitride containing hydrogen, silicon carbide, silicon carbide containing hydrogen, silicon oxide, boron nitride, boron nitride containing hydrogen, cerium oxide, aluminum oxide, zirconium oxide, titanium oxide, or magnesium fluoride, and forming thereon an alignment control layer of an organic insulating material, such as polyvinyl alcohol, polyimide, polyamide-imide, polyester-imide, polyparaxylylene, polyester, polycarbonate, polyvinyl acetal, polyvinyl chloride, polyvinyl acetate, polyamide, polystyrene, cellulose resin, melamine resin, urea resin, acrylic resin, or photoresist resin. Alternatively, it is also possible to use a single layer of inorganic insulating alignment control layer or organic insulating alignment control layer. An inorganic insulating alignment control layer may be formed by vapor deposition, while an organic insulating alignment control layer may be formed by applying a solution of an organic insulating material or a precursor thereof in a concentration of 0.1 to 20 wt. %, preferably 0.2-10 wt. %, by spinner coating, dip coating, screen printing, spray coating or roller coating, followed by curing or hardening under prescribed hardening condition (e.g., by heating). The insulating alignment control layer may have a thickness of ordinarily 30 Å-1 micron, preferably 30-3000 Å, further preferably 50-1000 Å. The two glass substrates 2 with transparent electrodes 3 (which may be inclusively referred to herein as "electrode plates") and further with insulating alignment control layers 4 thereof are held to have a prescribed (but arbitrary) gap with a spacer 5. For example, such a cell structure with a prescribed gap may be formed by sandwiching spacers of silica beads or alumina beads having a prescribed diameter with two glass plates, and then sealing the periphery thereof with, e.g., an epoxy adhesive. Alternatively, a polymer film or glass fiber may also be used as a spacer. Between the two glass plates, a liquid crystal assuming a chiral smectic phase is sealed up to provide a liquid crystal layer 1 in a thickness of generally 0.5 to 20 microns, preferably 1 to 5 microns.

The ferroelectric liquid crystal provided by the composition of the present invention may desirably assume a SmC* phase (chiral smectic C phase) in a wide temperature range including room temperature (particularly, broad in a lower temperature side) and also shows high-speed responsiveness, a smaller temperature-dependence of response speed and wide drive voltage margin when contained in a device.

Particularly, in order to show a good alignment characteristic to form a uniform monodomain, the ferroelectric liquid crystal may show a phase transition series comprising isotropic phase—Ch phase (cholesteric phase)—SmA phase (smectic A phase)—SmC* phase (chiral smectic C phase) on temperature decrease.

The transparent electrodes 3 are connected to the external power supply 7 through the lead wires 6. Further, outside the glass substrates 2, polarizers 8 are applied. The device shown in FIG. 1 is of a transmission type and is provided with a light source 9.

Figure 2:
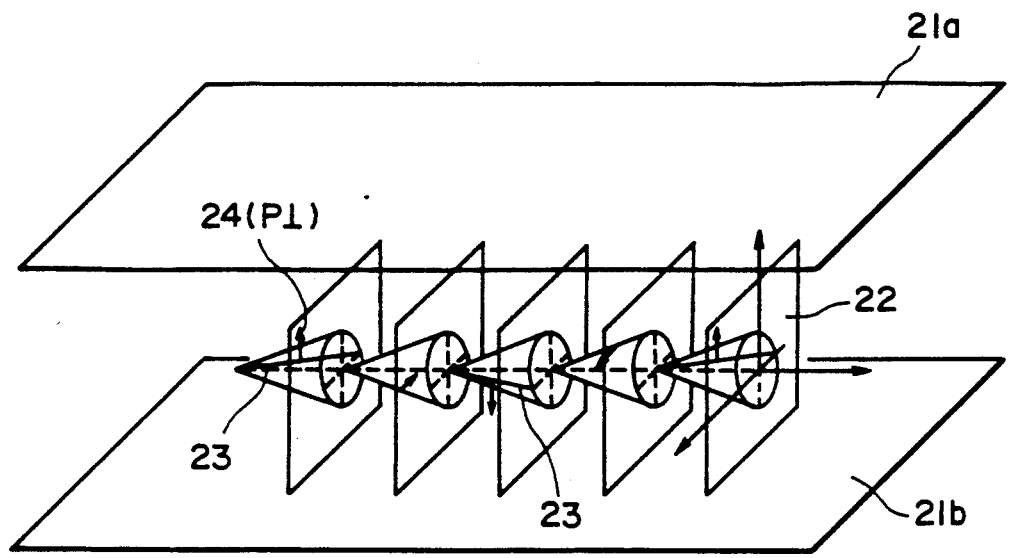
FIGS. 2 and 3 are schematic perspective views of a device cell embodiment for illustrating the operation principle of a liquid crystal device utilizing ferroelectricity of a liquid crystal composition.

FIG. 2 is a schematic illustration of a liquid crystal cell (device) utilizing ferroelectricity for explaining operation thereof. Reference numerals 21a and 21b denote substrates (glass plates) on which a transparent electrode of, e.g., $In_2O_3$, $SnO_2$, ITO (indium-tin-oxide), etc., is disposed, respectively. A liquid crystal of an SmC*-phase (chiral smectic C phase) or SmH*-phase (chiral smectic H phase) in which liquid crystal molecular layers 22 are aligned perpendicular to surfaces of the glass plates is hermetically disposed therebetween. Full lines 23 show liquid crystal molecules. Each liquid crystal molecule 23 has a dipole moment (P⊥) 24 in a direction perpendicular to the axis thereof. The liquid crystal molecules 23 continuously form a helical structure in the direction of extension of the substrates. When a voltage higher than a certain threshold level is applied between electrodes formed on the substrates 21a and 21b, a helical structure of the liquid crystal molecule 23 is unwound or released to change the alignment direction of respective liquid crystal molecules 23 so that the dipole moments (P⊥) 24 are all directed in the direction of the electric field. The liquid crystal molecules 23 have an elongated shape and show refractive anisotropy between the long axis and the short axis thereof. Accordingly, it is easily understood that when, for instance, polarizers arranged in a cross nicol relationship, i.e., with their polarizing directions crossing each other, are disposed on the upper and the lower surfaces of the glass plates, the liquid crystal cell thus arranged functions as a liquid crystal optical modulation device of which optical characteristics vary depending upon the polarity of an applied voltage.

Figure 3:
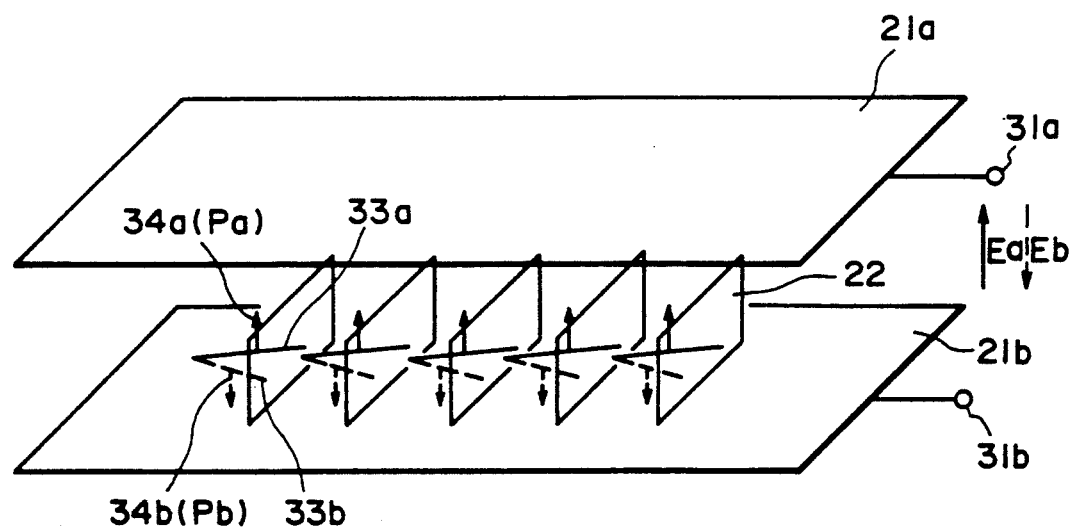

Further, when the liquid crystal cell is made sufficiently thin (e.g., less than about 10 microns), the helical structure of the liquid crystal molecules is unwound to provide a non-helical structure even in the absence of an electric field, whereby the dipole moment assumes either of the two states, i.e., Pa in an upper direction 34a or Pb in a lower direction 34b as shown in FIG. 3, thus providing a bistable condition. When an electric field Ea or Eb higher than a certain threshold level and different from each other in polarity as shown in FIG. 3 is applied to a cell having the above-mentioned characteristics by using voltage application means 31a and 31b, the dipole moment is directed either in the upper direction 34a or in the lower direction 34b depending on the vector of the electric field Ea or Eb. In correspondence with this, the liquid crystal molecules are oriented in either of a first stable state 33a and a second stable state 33b.

When the above-mentioned ferroelectric liquid crystal is used as an optical modulation element, it is possible to obtain two advantages. First is that the response speed is quite fast. Second is that the orientation of the liquid crystal shows bistability. The second advantage will be further explained, e.g., with reference to FIG. 3. When the electric field Ea is applied to the liquid crystal molecules, they are oriented in the first stable state 33a. This state is stably retained even if the electric field is removed. On the other hand, when the electric field Eb of which direction is opposite to that of the electric field Ea is applied thereto, the liquid crystal molecules are oriented to the second stable state 33b, whereby the directions of molecules are changed. This state is similarly stably retained even if the electric field is removed. Further, as long as the magnitude of the electric field Ea or Eb being applied is not above a certain threshold value, the liquid crystal molecules are placed in the respective orientation states.

Figure 4:
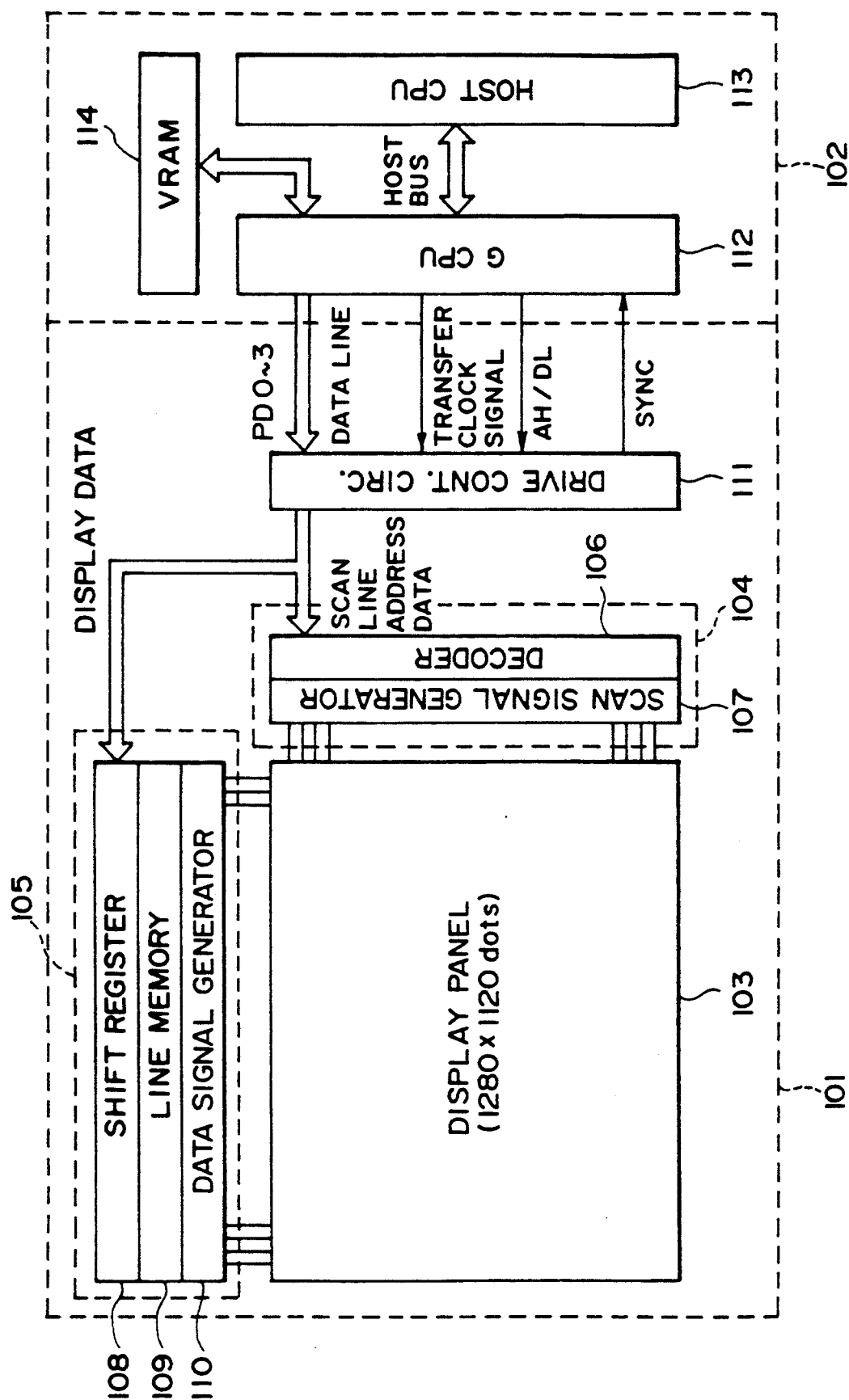
FIG. 4 is a block diagram showing a display apparatus comprising a liquid crystal device utilizing ferroelectricity of a liquid crystal composition and a graphic controller.
Figure 5:
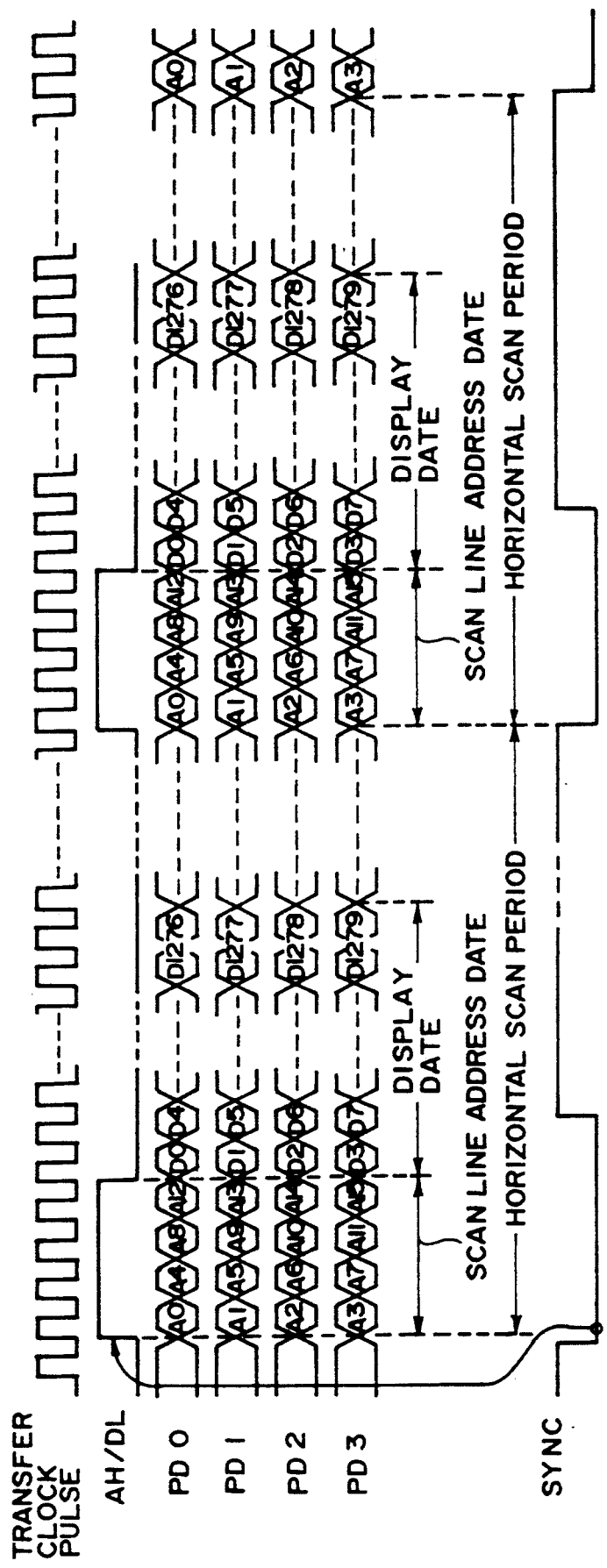
FIG. 5 is a time chart of image data communication showing time correlation between signal transfer and driving with respect to a liquid crystal display apparatus and a graphic controller.

Based on the arrangement and data format comprising image data accompanied with scanning line address data and by adopting communication synchronization using a SYNC signal as shown in FIGS. 4 and 5, there is provided a liquid crystal display apparatus of the present invention which uses the liquid crystal device according to the present invention as a display panel portion.

Referring to FIG. 4, the ferroelectric liquid crystal display apparatus 101 includes a graphic controller 102, a display panel 103, a scanning line drive circuit 104, a data line drive circuit 105, a decoder 106, a scanning signal generator 107, a shift resistor 108, a line memory 109, a data signal generator 110, a drive control circuit 111, a graphic central processing unit (GCPU) 112, a host central processing unit (host CPU) 113, and an image data storage memory (VRAM) 114.

Image data are generated in the graphic controller 102 in an apparatus body and transferred to a display panel 103 by signal transfer means shown in FIGS. 4 and 5. The graphic controller 102 principally comprises a CPU (central processing unit, hereinafter referred to as "GCPU") 112 and a VRAM (video-RAM, image data storage memory) 114 and is in charge of management and communication of image data between a host CPU 113 and the liquid crystal display apparatus (FLCD) 101. The control of the display apparatus is principally realized in the graphic controller 102. A light source is disposed at the back of the display panel 103.

Hereinbelow, the present invention will be explained more specifically with reference to examples. It is however to be understood that the present invention is not restricted to these examples.

EXAMPLE 1

2-(4-octylphenyl)-5-hexylbenzoxazole (Example Compound No. I-7) was synthesized through the following steps i) and ii).

Step i)

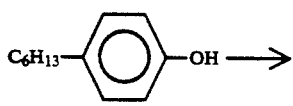

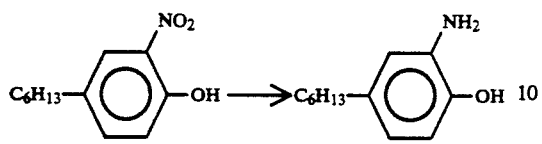

1.00 g (5.61 mM) of 4-hexylphenol was dissolved in a mixture solvent of 2.0 ml of benzene and 1.3 ml of acetic acid. To the solution, 0.62 ml (8.15 mM) of nitric acid (60%, density=1.38) was gradually added dropwise under cooling with iced water and stirring below 8° C. After the reaction, the reaction mixture was poured into water and extracted with ethyl acetate. The organic layer was dried with anhydrous sodium sulfate and subjected to reduced-pressure distillation into a solid. The solid was purified by silica gel column chromatography (eluent: toluene/hexane=½) to obtain 1.16 g of oily yellow 2-nitro-4-hexylphenol (Yield: 92.6%).

In a 50 ml-three-necked flask, 1.10 g (4.93 mM) of 2-nitro-4-hexylphenol, 0.30 g of activated carbon, 0.02 g of $FeCl_3 \cdot 6H_2O$ and 5 ml of ethanol were placed and heated to 55°–70° C. under stirring. To the mixture, 1.5 ml of 80% hydrazine hydrate was gradually added dropwise and heated to 70° C., followed by stirring for 30 min at 70°–75° C. After the reaction, the reaction mixture was filtered under heating to remove the activated carbon and the filtrate was poured into water to precipitate a crystal. The crystal was recovered by filtration, followed by drying under reduced pressure to obtain 0.78 g of 2-amino-4-hexylphenol (yield: 81.9%).

Step ii)

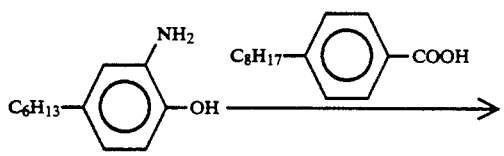

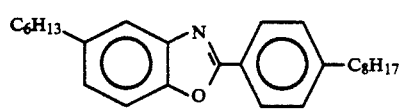

In a 50 ml-round-bottomed flask, 19 g of polyphosphoric acid, 0.30 g (1.55 mM) of 2-amino-4-hexylphenol and 0.37 g (1.58 mM) of 4-octylbenzoate acid were placed, followed by stirring for 3.5 hours at about 250° C. After the reaction, the reaction mixture was poured into water to precipitate a crystal. The crystal was recovered by filtration and was washed with 10% $K_2CO_3$. The crystal was dissolved in ethyl acetate and washed with water, followed by drying with anhydrous sodium sulfate and distilling-off of the solvent. The resultant residue was purified by silica gel column chromatography (eluent: toluene/hexane=½) to obtain 0.17 g of 2-(4-octylphenyl)-5-hexylbenzoxazole (yield: 28.0%).

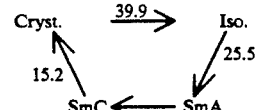

Cryst.: crystal,

SmC: smetic C phase,

SmA: smetic A phase, and

Iso.: isotropic phase.

EXAMPLE 2

2-(4-decyloxyphenyl)-5-octylbenzoxazole (Example Compound No. 1-73) was synthesized through the following steps i) and ii).

Step i)

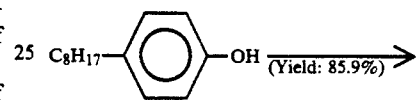

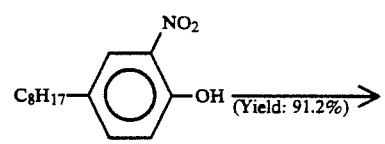

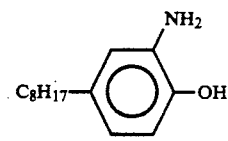

2-amino-4-octylphenol was synthesized through the above reaction schemes with the indicated yields in the same manner as in Step i) of Example 1.

Step ii)

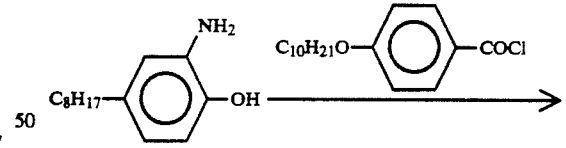

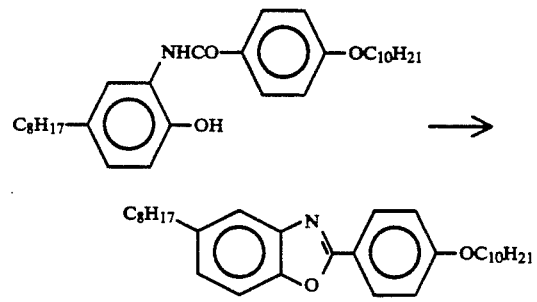

In a 50 ml-three-necked flask, 0.50 g (2.43 mM) of 2-amino-4-octylphenol, 0.82 g (2.54 mM) of 4-decyloxybenzoyl chloride and 20 ml of dioxane were placed and heated. To the mixture, 0.88 ml of pyridine was gradually added dropwise at around 90° C. under stirring, followed by further stirring for 35 minutes at around 90° C. After the reaction, the reaction mixture was poured into water to precipitate a crystal. The crystal was recovered by filtration and washed with water, followed by recrystallization from hydrous acetone to obtain 1.06 g of 2-(4-decyloxybenzoylamino)-4-octylphenol (yield: 90.4%).

In a 30 ml-round-bottomed flask, 1.00 g (2.08 mM) of 2-(4-decyloxybenzoylamino)-4-octylphenol, 0.07 g (0.68 mM) of p-toluenesulfonic acid monohydrate and 10 ml of o-dichlorobenzene were placed, followed by stirring for 37 min. at 188°-193° C. After the reaction, o-dichlorobenzene was distilled off under reduced pressure. The residue was purified by silica gel column chromatography (eluent: toluene) to obtain 0.59 g of 2-(4-decyloxyphenyl)-5-octylbenzoxazole (yield: 61.3%).

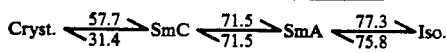

EXAMPLE 3

2-(4-hexyloxyphenyl)-5-butylbenzoxazole (Example Compound No. 1-58) was synthesized through the following reaction schemes with the indicated yields in a similar manner as in Example 2.

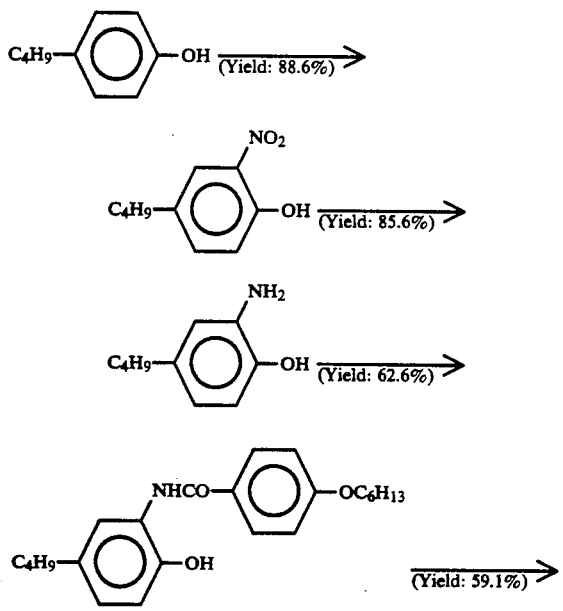

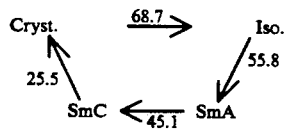

EXAMPLE 4

2-[4-(2-fluorooctyloxy)phenyl]-5octylbenzoxazole (Example Compound No. 1-76) was synthesized through the following steps i)–iii).

Step i)

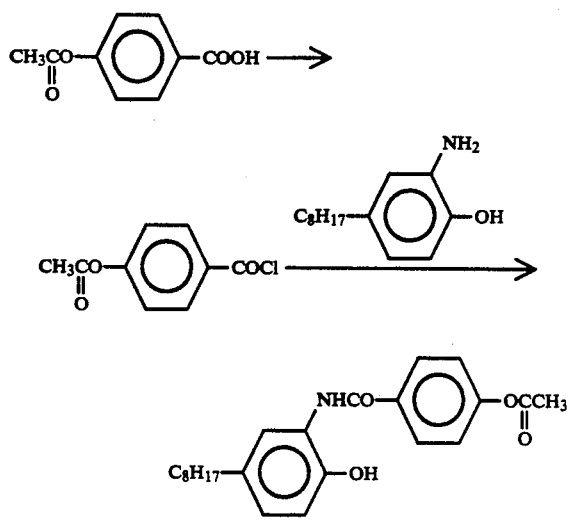

In a 20 ml-round-bottomed flask, 2.90 g (16.1 mM) of 4-acetoxybenzoic acid and 3.7 ml of thionyl chloride were placed. To the mixture, two drops of N,N-dimethylformamide was added at room temperature under stirring, followed by heat-refluxing for 20 minutes under stirring. After the reaction, dry benzene was added to the reaction mixture, followed by distilling-off of excessive thionyl chloride together with benzene. The above operation was repeated two times to obtain 4-acetoxybenzoic acid chloride. Then, in a 100 ml-round-bottomed flask, the above-prepared 4-acetoxybenzoic acid chloride, 3.10 g (15.1 mM) of 2-amino-4-octylphenol and 40 ml of dioxane were placed and heated. To the mixture, 5.5 ml of pyridine was added dropwise at 80°-84° C. under stirring, followed by further stirring for 20 minutes at 85°-88.5° C. After the reaction, the reaction mixture was cooled on an ice bath and poured into about 200 ml of ice water to precipitate a crystal. The crystal was recovered by filtration and washed with water, followed by recrystallization from methanol to obtain 4.10 g of 2-(4-acetoxybenzoylamino)-4-octylphenol (Yield: 70.8%).

Step ii)

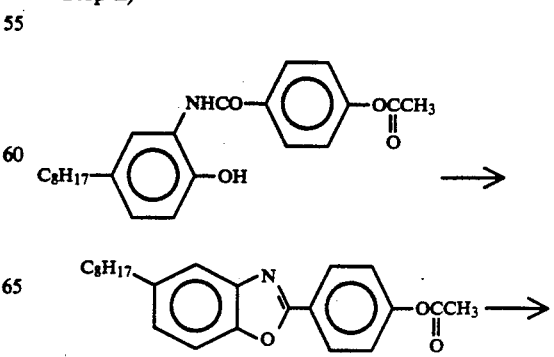

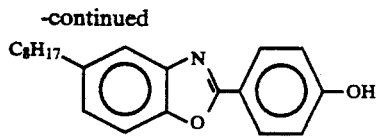

In a 200 ml-round-bottomed flask, 4.00 g (10.4 mM) of 2-(4-acetoxybenzoylamino)-4-octylphenol, 0.40 g of p-toluenesulfonic acid monohydrate and 40 ml of o-dichlorobenzene were placed, followed by stirring for 1 hour at 188°–192° C. After the reaction, odichlorobenzene in the reaction mixture was distilled off under reduced pressure. To the residue, 1.98 g (30.0 mM) of potassium hydroxide and 60 ml of ethanol was added and stirred for 1 hour on a water bath kept at about 75° C. After the reaction, ethanol in the reaction mixture was distilled off under reduced pressure. Water was added to the resultant residue, followed by addition of 6.0 ml (34.0 mM) of concentrated hydrochloric acid under stirring on an ice bath to precipitate a crystal. The crystal was recovered by filtration and washed with water, followed by recrystallization from ethanol to obtain 2.70 g of 2-(4-hydroxyphenyl)-5-octylbenzoxazole (Yield: 80.0%).

Step iii)

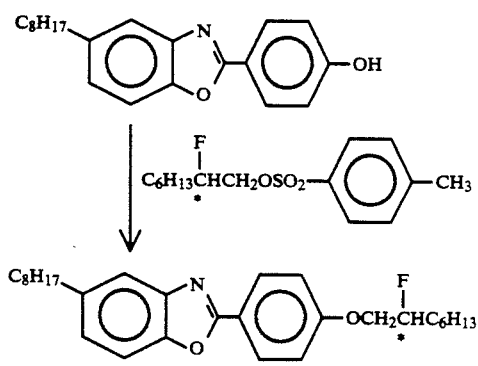

In a 30 ml-round-bottomed flask, 0.50 g (1.55 mM) of 2-(4-hydroxyphenyl)-5-octylbenzoxazole, 0.20 g (3.03 mM) of potassium hydroxide was 5 ml of n-butanol were placed and heated to dissolve. To the solution on an oil bath kept at about 90° C., 0.90 g (2.59 mM) of 2-fluorooctyl-p-toluenesulfonate obtained from (−)-2-fluorooctanol was gradually added, followed by heat-refluxing for 1 hour and 40 minutes under stirring. After the reaction, the reaction mixture was cooled to precipitate a crystal. The crystal was recovered by filtration and washed with water to dissolve in toluene, followed by drying with anhydrous sodium sulfate and distilling-off of toluene. The residue was purified by silica gel column chromatography (eluent: toluene) and recrystallized from acetone to obtain 0.41 g of 2-[4-(2-fluorooctyloxy)phenyl]-5-octylbenzoxazole (Yield: 58.3%).

Phase transition temperature (°C.)

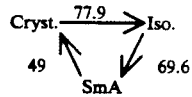

EXAMPLE 5

2-(4-decyloxyphenyl)-5-octyloxybenzoxazole (Example Compound No. 1-114) was synthesized through the following reaction schemes.

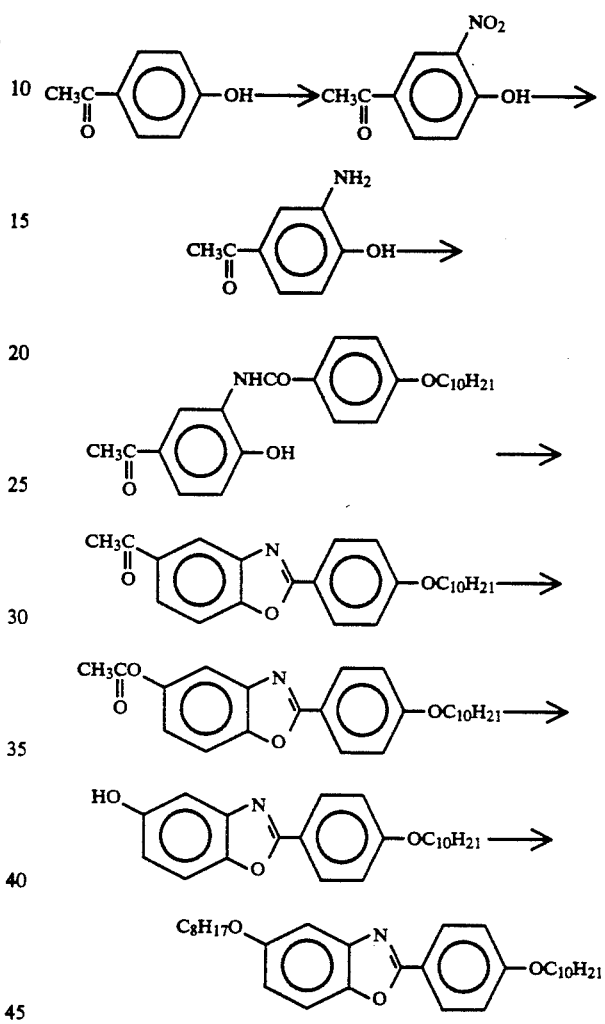

5.00 g (36.7 ml) of 4-acetylphenol was dissolved in 50 ml of sulfuric acid. To the solution, 3.10 ml (40.7 mM) of nitric acid (60%, density=1.38) was gradually added dropwise under stirring at 2°–10° C. on an ice bath, followed by stirring at 2°–10° C. after the addition. After the reaction, the reaction mixture was poured into ice water to precipitate a crystal. The crystal was recovered by filtration and washed with water, followed by recrystallization from methanol to obtain 5.84 g of 2-nitro-4-acetylphenol (Yield: 79.8%).

In a 300 ml-three-necked flask, 5.00 g (27.6 mM) of 2-nitro-4-acetylphenol was 75 ml of 2N-sodium hydroxide aqueous solution were placed. To the mixture, a solution of 25.00 g of sodium hydrosulfite ($Na_2S_2O_4$) in 75 ml of water was added dropwise in 10 minutes, followed by stirring for 20 minutes at room temperature to precipitate a crystal. The crystal was recovered by filtration and recrystallized from a mixture solvent (methanol-water) to obtain 1.63 g of 2-amino-4-acetylphenol (Yield: 39.1%).

Then, 3.11 g of 2-(4-decyloxyphenyl)-5-acetylbenzoxazole was obtained from 1.60 g (10.6 mM) of 2- amino-4-acetylphenol in the same manner as in Step ii) of Example 2 (Yield: 74.7%).

In a 50 ml-round-bottomed flask, 1.50 g of (3.81 mM) of 2-(4-decyloxyphenyl)-5-acetylbenzoxazole was dissolved in 10 ml of dichloromethane, followed by successive addition of 0.66 g of (3.82 mM) of m-chloroperbenzoic acid and 0.40 g (4.00 mM) of potassium hydrogencarbonate and heat-refluxing for 7 hours and 40 minutes under stirring. After cooling to room temperature, 0.33 g (1.91 mM) of m-chloroperbenzoic acid and 0.20 g (2.00 mM) of potassium hydrogencarbonate was successively added, followed by heat-refluxing for 12 hours under stirring. After the reaction, the insoluble was filtered off and the filtrate was subjected to reduced pressure distillation to obtain a residue. The residue was purified by silica gel column chromatography (eluent: toluene/ethyl acetate=100/1) to obtain 2-(4-decyloxyphenyl)-5-acetoxybenzoxazole. Then, 0.51 g (7.73 mM) of potassium hydroxide was dissolved in 50 ml of ethanol under heating. To the solution, the above-prepared 2-(4-decyloxyphenyl)-5-acetoxybenzoxazole was added, followed by stirring for 30 minutes at about 60° C. After the reaction, ethanol in the reaction mixture was distilled off under reduced pressure. To the resultant residue, 50 ml of water was added, followed by addition of 0.7 ml of hydrochloric acid under stirring on an ice bath to precipitate a crystal. The crystal was recovered by filtration and washed with water, followed by recrystallization from methanol to obtain 0.27 g of 2-(4-decyloxyphenyl)-5-hydroxybenzoxazole (Yield: 19.3%).

In a 20 ml-round-bottomed flask, 0.25 g (0.68 mM) of 2-(4-decyloxyphenyl)-5-hydroxybenzoxazole, 0.08 g (1.21 mM) of potassium hydroxide and 3 ml of butanol were placed and heated to provide a solution. To the solution, 0.18 ml (1.00 mM) of octyl iodide was added, followed by heat-refluxing for 5 hours and 40 minutes under stirring. After the reaction, the solvent in the reaction mixture was distilled off under reduced pressure. To the residue, ethyl acetate and water were added, followed by stirring at room temperature. The organic layer was successively washed with 2%-sodium thiosulfate aqueous solution and water, followed by drying with anhydrous sodium sulfate and reduced pressure distillation. The resultant residue was purified by silica gel column chromatography (eluent: toluene) and recrystallized from a mixture solvent (acetone-methanol) to obtain 0.17 g of 2-(4-decyloxyphenyl)-5-octyloxybenzoxazole (Yield: 52.1%).

Phase transition temperature (°C.)

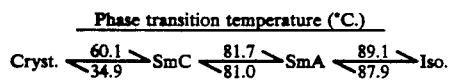

EXAMPLE 6

A liquid crystal composition A was prepared by mixing the following compounds in respectively indicated proportions.

| Structural formula | wt. parts |
|---|---|
| $C_6H_{13}O$—⟨phenyl⟩—⟨pyrimidine(N,N)⟩—$C_8H_{17}$ | 46.14 |
| $C_9H_{19}O$—⟨phenyl⟩—⟨pyrimidine(N,N)⟩—$C_8H_{17}$ | 23.07 |
| $C_8H_{17}O$—⟨phenyl⟩—⟨pyrimidine(N,N)⟩—$C_{10}H_{21}$ | 11.54 |
| $C_3H_7$—⟨cyclohexyl-H⟩—CO-O—⟨phenyl⟩—⟨pyrimidine(N,N)⟩—$C_{11}H_{23}$ | 3.56 |
| $C_4H_9$—⟨cyclohexyl-H⟩—CO-O—⟨phenyl⟩—⟨pyrimidine(N,N)⟩—$C_{11}H_{23}$ | 3.56 |
| $C_5H_{11}$—⟨cyclohexyl-H⟩—CO-O—⟨phenyl⟩—⟨pyrimidine(N,N)⟩—$C_{11}H_{23}$ | 7.13 |
| $C_{12}H_{25}$—⟨pyrimidine(N,N)⟩—⟨phenyl⟩—$OCH_2\overset{*}{C}HC_6H_{13}$ (with F) | 2.50 |
| $C_{10}H_{21}$—⟨pyrimidine(N,N)⟩—⟨phenyl⟩—$OCH_2\overset{*}{C}HC_6H_{13}$ (with F) | 2.50 |

The liquid crystal composition A was further mixed with the following Example Compound No. I-58 in the proportions indicated below to provide a liquid crystal composition B.

| Ex. Comp. No. | Structural formula | wt. parts |
|---|---|---|
| I-58 | $C_4H_9$—⟨benzoxazole⟩—⟨phenyl⟩—$OC_6H_{13}$ | 5 |
| | Composition A | 95 |

The liquid crystal composition B showed the following phase transition series.

Phase transition temperature (°C.)

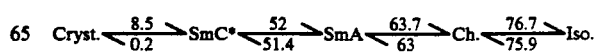

Ch.: cholesteric phase, and
SmC*: chiral smectic C phase.

EXAMPLE 7

Two 0.7 mm-thick glass plates were provided and respectively coated with an ITO film to form an electrode for voltage application, which was further coated with an insulating layer of vapor-deposited $SiO_2$. On the insulating layer, a 0.2%-solution of silane coupling agent (KBM-602, available from Shinetsu Kagaku K.K.) in isopropyl alcohol was applied by spinner coating at a speed of 2000 rpm for 15 seconds and subjected to hot curing treatment at 120° C. for 20 min.

Further, each glass plate provided with an ITO film and treated in the above described manner was coated with a 1.5%-solution of polyimide resin precursor (SP-510, available from Toray K.K.) in dimethylacetoamide by a spinner coater rotating at 2000 rpm for 15 seconds. Thereafter, the coating film was subjected to heat curing at 300° C. for 60 min. to obtain about 250 Å-thick film. The coating film was rubbed with acetate fiber-planted cloth. The thus treated two glass plates were washed with isopropyl alcohol. After alumina beads with an average particle size of 2.0 microns were dispersed on one of the glass plates, the two glass plates were applied to each other with a bonding sealing agent (Lixon Bond, available from Chisso K.K.) so that their rubbed directions were parallel to each other and heated at 100° C. for 60 min. to form a blank cell. The cell gap was found to be about 2 microns as measured by a Berek compensator.

Then, the liquid crystal composition B prepared in Example 7 was heated into an isotropic liquid, and injected into the above prepared cell under vacuum and, after sealing, was gradually cooled at a rate of 20° C./hour to 25° C. to prepare a ferroelectric liquid crystal device.

The ferroelectric liquid crystal device was subjected to measurement of the magnitude of spontaneous polarization Ps and an optical response time (time from voltage application until the transmittance change reaches 90% of the maximum under the application of a peak-to-peak voltage Vpp of 20 V in combination with right-angle cross-nicol polarizers).

The results are shown below.

|                              | 10° C. | 30° C. | 45° C. |
|------------------------------|--------|--------|--------|
| Response time (μsec)         | 504    | 226    | 122    |
| Ps (nC/cm²)                  | 3.79   | 2.57   | 1.27   |

COMPARATIVE EXAMPLE 1

2-(4-hexyloxyphenyl)-5-methylbenzoxazole was synthesized through the following reaction schemes with the indicated yields in the same manner as in Example 2.

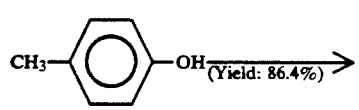

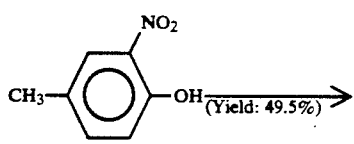

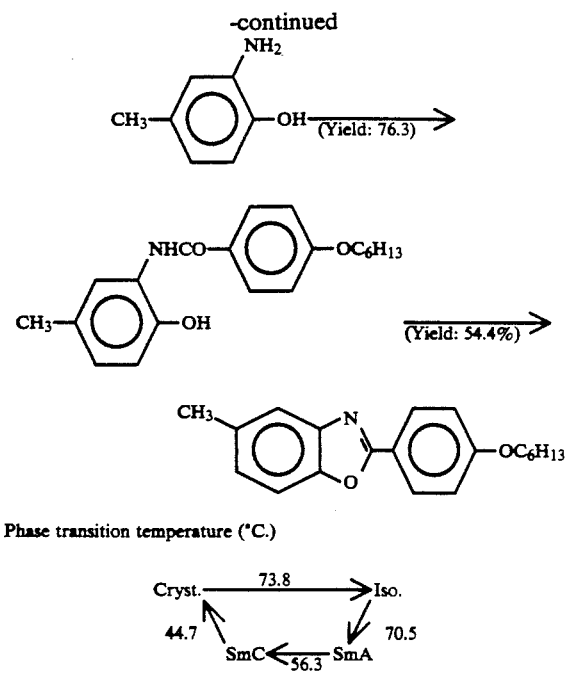

Phase transition temperature (°C.)

A liquid crystal composition C was prepared by mixing the following compounds prepared above with the liquid crystal composition A in the respectively indicated proportions.

| Structural formula | wt. parts |
|---|---|
| 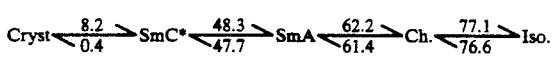 | 5 |
| Composition A | 95 |

The liquid crystal composition C showed the following phase transition series.

Phase transition temperature (°C.)

$$Cryst \xrightarrow[0.4]{8.2} SmC^* \xrightarrow[47.7]{48.3} SmA \xrightarrow[61.4]{62.2} Ch. \xrightarrow[76.6]{77.1} Iso.$$

A ferroelectric liquid crystal device was prepared in the same manner as in Example 7 except for using the composition C. The ferroelectric liquid crystal device was subjected to measurement of the magnitude of spontaneous polarization Ps and response time in the same manner as in Example 7, whereby the following results were obtained.

|                              | 10° C. | 30° C. | 45° C. |
|------------------------------|--------|--------|--------|
| Response time (μsec)         | 507    | 224    | 49     |
| Ps (nC/cm²)                  | 3.31   | 2.22   | 0.50   |

As is apparent from Example 3 and Comparative Example 1, the mesomorphic compound (Ex. Comp. No. 1-58) according to the present invention showed a wider temperature range of a smectic C phase than that of the 2-phenylbenzoxazole derivative disclosed in "Mol. Cryst. Liq. Cryst.", 37, 44 (1976). Further, as is understood from Examples 6 and 7 and Comparative Example 1, a ferroelectric chiral smectic liquid crystal composition containing the above compound (Ex. Comp. No. 1-58) of the present invention showed a wider temperature range of a chiral smectic C phase and provided a smaller temperature-dependence of response speed compared with those of the above-mentioned 2-phenylbenzoxazole derivative.

EXAMPLE 8

A liquid crystal composition D was prepared by mixing the following Example Compounds No. 1-73 prepared in Example 2 in the indicated proportions with the liquid crystal composition A prepared in Example 6.

| Ex. Comp. No. | Structural formula | wt. parts |
|---|---|---|
| 1-73 | $C_8H_{17}$—[benzoxazole]—[phenyl]—$OC_{10}H_{21}$ | 5 |
| | Composition A | 95 |

The liquid crystal composition D showed the following phase transition series.

Phase transition temperature (°C.)

$$\text{Cryst.} \xrightarrow{9.2} \text{SmC*} \xrightarrow{56.2} \text{SmA} \xrightarrow{67.1} \text{Ch.} \xrightarrow{77.1} \text{Iso.}$$

A ferroelectric liquid crystal device was prepared in the same manner as in Example 7 except for using the composition D. The ferroelectric liquid crystal device was subjected to measurement of the magnitude of spontaneous polarization Ps and response time in the same manner as in Example 7, whereby the following results were obtained.

|  | 10° C. | 30° C. | 45° C. |
|---|---|---|---|
| Response time (μsec) | 498 | 228 | 141 |
| Ps (nC/cm$^2$) | 3.79 | 2.71 | 1.64 |

EXAMPLE 9

A liquid crystal composition E was prepared by mixing the following compounds in the respectively indicated proportions.

| Structural formula | wt. parts |
|---|---|
| $C_7H_{15}$—[pyrimidine]—[phenyl]—$OC_9H_{19}$ | 12 |
| $C_{11}H_{23}$—[pyrimidine]—[phenyl]—$OC_6H_{13}$ | 10 |
| $C_8H_{17}$—[pyrimidine]—[phenyl]—$O\text{-(CH}_2)_3^*\text{CH(CH}_3)\text{C}_2\text{H}_5$ | 10 |
| $C_{10}H_{21}$—[pyrimidine]—[phenyl]—$O\text{-(CH}_2)_2^*\text{CH(CH}_3)\text{OCH}_3$ | 3 |
| $C_8H_{17}$—[pyrimidine]—[phenyl]—[phenyl]—$OC_6H_{13}$ | 8 |
| $C_6H_{13}O$—[phenyl]—$OC(=O)$—[naphthyl]—$OC_9H_{19}$ | 4 |
| $C_3H_7$—[cyclohexyl H]—$CO_2$—[phenyl]—[pyrimidine]—$C_{11}H_{23}$ | 6 |

-continued

| Structural formula | wt. parts |
|---|---|
| $C_8H_{17}$—[H]—CO-O—[⌬]—[N⌬N]—$C_{11}H_{23}$ | 2 |
| $C_5H_{11}$—[H]—CO-O—[⌬]—[N⌬N]—$C_{11}H_{23}$ | 8 |
| $C_{10}H_{21}O$—[⌬]—CO-O—[⌬]—$OCH_2\overset{*}{C}HC_2H_5$ (with $CH_3$ branch) | 15 |
| $C_4H_9$—[H]—$CH_2O$—[⌬]—[N⌬N]—$C_6H_{13}$ | 7 |
| $C_5H_{11}$—[H]—$CH_2O$—[⌬]—[N⌬N]—$C_6H_{13}$ | 7 |
| $C_9H_{19}O$—[⌬]—$OCH_2$—[⌬]—[⌬]—$C_7H_{15}$ | 4 |
| $C_6H_{13}\overset{*}{C}HO$—[⌬]—CO-O—[⌬]—[⌬]—$O\overset{*}{C}CHOC_4H_9$ (CH_3 branches) | 2 |
| $C_{12}H_{25}$—[N⌬N]—[⌬]—$O\overset{*}{C}\overset{Cl}{C}H$—$\overset{CH_3}{C}HC_2H_5$ | 2 |

The liquid crystal composition E was further mixed with the following Example Compounds in the proportions indicated below to provide a liquid crystal composition F. The ferroelectric liquid crystal device was subjected to measurement of response time in the same manner as in Example 7, whereby the following results were obtained.

| Ex. Comp. No. | Structural formula | wt. parts |
|---|---|---|
| 1-7 | $C_6H_{13}$—[benzoxazole]—[⌬]—$C_8H_{17}$ | 3 |
| 1-12 | $C_8H_{17}$—[benzoxazole]—[⌬]—$CH_2\overset{*}{C}HC_2H_5$ (CH_3) | 2 |
| 1-129 | $C_{11}H_{23}O$—[benzoxazole]—[⌬]—$OC_{13}H_{27}$ | 3 |
| | Composition E | 92 |

A ferroelectric liquid crystal device was prepared in the same manner as in Example 7 except for using the

|  | 10° C. | 25° C. | 40° C. |
|---|---|---|---|
| Response time (μsec) | 723 | 352 | 193 |

COMPARATIVE EXAMPLE 2

A ferroelectric liquid crystal device was prepared in the same manner as in Example 7 except that the liquid crystal composition E prepared in Example 9 was injected into a cell. The measured values of the response time of the device were as follows.

|  | 10° C. | 25° C. | 40° C. |
|---|---|---|---|
| Response time (μsec) | 784 | 373 | 197 |

EXAMPLE 10

A liquid crystal composition G was prepared by mixing the following example compounds in the indicated proportions with the liquid crystal composition E prepared in Example 9.

| Ex. Comp. No. | Structural formula | wt. parts |
|---|---|---|
| 1-18 | $C_{10}H_{21}$–[benzoxazole]–[phenyl]–$C_{10}H_{21}$ | 3 |
| 1-45 | $C_4H_9\overset{*}{C}H(F)CH_2O$–[benzoxazole]–[phenyl]–$C_8H_{17}$ | 2 |
| 1-123 | $C_{10}H_{21}O$–[benzoxazole]–[phenyl]–F | 2 |
| Composition E | | 93 |

A ferroelectric liquid crystal device was prepared in the same manner as in Example 7 except that the above liquid crystal composition G was used, and the device was subjected to measurement of optical response time. The results of the measurement are shown below.

|  | 10° C. | 25° C. | 40° C. |
|---|---|---|---|
| Response time (μsec) | 681 | 335 | 184 |

EXAMPLE 11

A liquid crystal composition H was prepared by mixing the following compounds in the respectively indicated proportions.

| Structural formula | wt. parts |
|---|---|
| $C_8H_{17}$–[pyrimidine]–[phenyl]–$OC_6H_{13}$ | 10 |
| $C_8H_{17}$–[pyrimidine]–[phenyl]–$OC_9H_{19}$ | 5 |
| $C_{10}H_{21}$–[pyrimidine]–[phenyl]–$OCOC_8H_{17}$ | 7 |
| $C_{10}H_{21}$–[pyrimidine]–[phenyl]–$O(CH_2)_3\overset{CH_3}{\underset{|}{C}}HOC_3H_7$ | 7 |

-continued

| Structural formula | wt. parts |
|---|---|
| C₁₂H₂₅–[pyrazine]–[phenyl]–O(CH₂)ₙCH(CH₃)OCH₃ | 6 |
| C₅H₁₁–[pyrazine]–[phenyl]–[phenyl]–C₆H₁₃ | 5 |
| C₇H₁₅–[pyrazine]–[phenyl]–[phenyl]–C₆H₁₃ | 5 |
| C₄H₉–[cyclohexyl-H]–COO–[phenyl]–[pyrazine]–C₁₂H₂₅ | 8 |
| C₃H₇–[cyclohexyl-H]–COO–[phenyl]–[pyrazine]–C₁₀H₂₁ | 8 |
| C₉H₁₉O–[phenyl]–COO–[phenyl]–OC₅H₁₁ | 20 |
| C₈H₁₇–[phenyl]–COO–[phenyl]–[phenyl]–OCH₂CH*(CH₃)C₂H₅ | 5 |
| C₈H₁₇–[phenyl]–OCO–[phenyl]–[phenyl]–CH*(CH₃)OCOC₆H₁₃ | 5 |
| C₆H₁₃–[phenyl]–OCH₂–[phenyl]–[phenyl]–C₇H₁₅ | 6 |
| C₁₂H₂₅–[pyridine]–[phenyl]–OCH₂CH*(F)C₆H₁₃ | 3 |

The liquid crystal composition H was further mixed with the following Example Compounds in the proportions indicated below to provide a liquid crystal composition I.

| Ex. Comp. No. | Structural formula | wt. parts |
|---|---|---|
| 1-2 |  C₄H₉–[benzoxazole]–[phenyl]–C₁₀H₂₁ | 3 |

-continued

| Ex. Comp. No. | Structural formula | wt. parts |
|---|---|---|
| 1-29 | $C_{10}H_{21}$—[benzoxazole]—[phenyl]—$CF_3$ | 2 |
| 1-61 | $C_5H_{11}$—[benzoxazole]—[phenyl]—$OC_7H_{15}$ | 3 |
| Composition H | | 92 |

A ferroelectric liquid crystal device was prepared in the same manner as in Example 7 except that the above liquid crystal composition I was used, and the device was subjected to measurement of optical response time and observation of switching states. In the device, a monodomain with a good and uniform alignment characteristic was observed. The results of the measurement are shown below.

| | 10° C. | 25° C. | 40° C. |
|---|---|---|---|
| Response time (μsec) | 576 | 284 | 145 |

Further, when the device was driven, a clear switching action was observed, and good bistability was shown after the termination of the voltage application.

COMPARATIVE EXAMPLE 3

A ferroelectric liquid crystal device was prepared in the same manner as in Example 7 except that the liquid crystal composition H prepared in Example 11 was injected into a cell. The measured values of the response time of the device were as follows.

| | 10° C. | 25° C. | 40° C. |
|---|---|---|---|
| Response time (μsec) | 653 | 317 | 159 |

EXAMPLE 12

A liquid crystal composition J was prepared by mixing the following example compounds in the indicated proportions with the liquid crystal composition H prepared in Example 11.

| Ex. Comp. No. | Structural formula | wt. parts |
|---|---|---|
| 1-46 | $C_9H_{19}O$—[benzoxazole]—[phenyl]—$C_{12}H_{25}$ | 2 |
| 1-78 | $C_8H_{17}$—[benzoxazole]—[phenyl]—$OCH_2\overset{CH_3}{\underset{|}{C}H}C_2H_5$ | 3 |
| 1-88 | $C_{12}H_{25}$—[benzoxazole]—[phenyl]—$OC_{10}H_{21}$ | 3 |
| Composition H | | 92 |

A ferroelectric liquid crystal device was prepared in the same manner as in Example 7 except that the above liquid crystal composition J was used, and the device was subjected to measurement of optical response time and observation of switching states. In the device, a monodomain with a good and uniform alignment characteristic was observed. The results of the measurement are shown below.

| | 10° C. | 25° C. | 40° C. |
|---|---|---|---|
| Response time (μsec) | 583 | 287 | 149 |

EXAMPLE 13

A liquid crystal composition K was prepared by mixing the following example compounds in the indicated proportions with the liquid crystal composition H prepared in Example 11.

| Ex. Comp. No. | Structural formula | wt. parts |
|---|---|---|
| 1-68 | $C_7H_{15}$-[benzoxazole]-[phenyl]-$OCH_2CH_2CH_2CHCH_3$ with $CH_3$ branch | 3 |
| 1-103 | $C_6H_{13}O$-[benzoxazole]-[phenyl]-$OC_{10}H_{21}$ | 2 |
| 1-112 | $C_8H_{17}O$-[benzoxazole]-[phenyl]-$OC_8H_{17}$ | 2 |
| Composition H | | 93 |

A ferroelectric liquid crystal device was prepared in the same manner as in Example 7 except that the above liquid crystal composition K was used, and the device was subjected to measurement of optical response time and observation of switching states. In the device, a monodomain with a good and uniform alignment characteristic was observed. The results of the measurement are shown below.

|  | 10° C. | 25° C. | 40° C. |
|---|---|---|---|
| Response time (μsec) | 591 | 293 | 150 |

EXAMPLE 14

A liquid crystal composition L was prepared by mixing the following compounds in the respectively indicated proportions.

| Structural formula | wt. parts |
|---|---|
| $C_9H_{19}$-[pyrimidine]-[phenyl]-$OC_9H_{19}$ | 6 |
| $C_{10}H_{21}$-[pyrimidine]-[phenyl]-$OC_8H_{17}$ | 6 |
| $C_8H_{17}$-[pyridine]-[phenyl]-$O(CH_2)_3$*$CHC_2H_5$ with $CH_3$ branch | 7 |
| $C_{11}H_{23}O$-[pyrimidine]-[phenyl]-$O(CH_2)_2$*$CHC_2H_5$ with $CH_3$ branch | 14 |
| $C_{10}H_{21}$-[pyridine]-[phenyl]-$C_6H_{13}$ | 8 |
| $C_6H_{13}$-[pyrimidine]-[phenyl]-[phenyl]-$C_4H_9$ | 4 |
| $C_8H_{17}$-[phenyl]-[pyridine]-[phenyl]-$OC_5H_{11}$ | 2 |

-continued
| Structural formula | wt. parts |
|---|---|
| 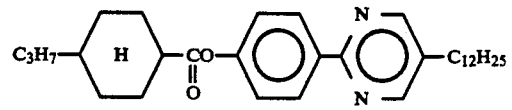 | 10 |
| 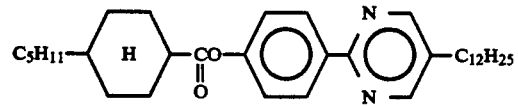 | 5 |
| 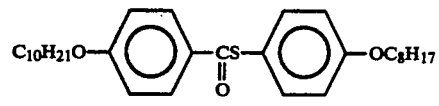 | 10 |
| 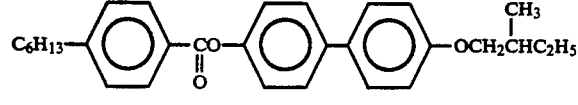 | 7 |
| 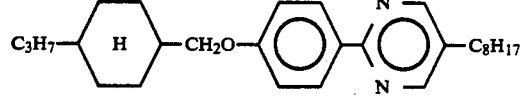 | 7 |
| 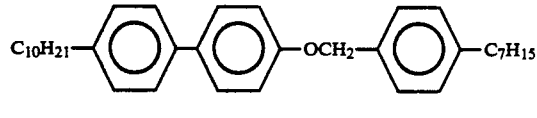 | 5 |
| 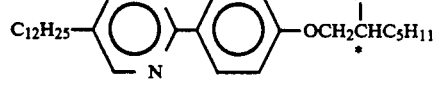 | 2 |
| 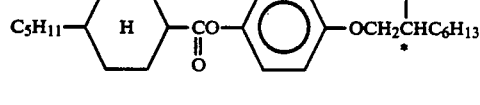 | 2 |
| 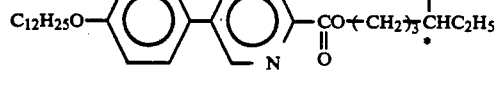 | 2 |
| 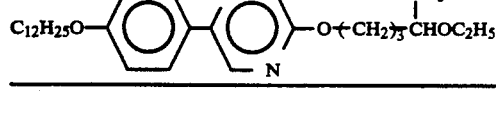 | 3 |
The liquid crystal composition L was further mixed with the following Example Compounds in the proportions indicated below to provide a liquid crystal composition M.
| Ex. Comp. No. | Structural formula | wt. parts |
|---|---|---|
| 1-48 | 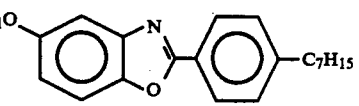 | 3 |

| Ex. Comp. No. | Structural formula | wt. parts |
|---|---|---|
| 1-100 | C$_6$H$_{13}$O—[benzoxazole]—[phenyl]—O(CH$_2$)$_3$*CH(CH$_3$)C$_2$H$_5$ | 2 |
| 1-110 | C$_8$H$_{17}$O—[benzoxazole]—[phenyl]—OC$_7$H$_{15}$ | 2 |
| Composition L | | 93 |

A ferroelectric liquid crystal device was prepared in the same manner as in Example 7 except that the above liquid crystal composition M was used, and the device was subjected to measurement of optical response time and observation of switching states. In the device, a monodomain with a good and uniform alignment characteristic was observed. The results of the measurement are shown below.

|  | 10° C. | 25° C. | 40° C. |
|---|---|---|---|
| Response time (μsec) | 616 | 318 | 173 |

COMPARATIVE EXAMPLE 4

A ferroelectric liquid crystal device was prepared in the same manner as in Example 7 except that the liquid crystal composition L prepared in Example 14 was injected into a cell. The measured values of the response time of the device were as follows.

|  | 10° C. | 25° C. | 40° C. |
|---|---|---|---|
| Response time (μsec) | 668 | 340 | 182 |

EXAMPLE 15

A liquid crystal composition N was prepared by mixing the following example compounds in the indicated proportions with the liquid crystal composition L prepared in Example 14.

was subjected to measurement of optical response time. The results of the measurement are shown below.

|  | 10° C. | 25° C. | 40° C. |
|---|---|---|---|
| Response time (μsec) | 572 | 297 | 162 |

As is apparent from the results shown in the above Examples 9–15, the ferroelectric liquid crystal devices containing the liquid crystal compositions F, G, I, J. K, M and N showed an improved low-temperature operation characteristic, a high-speed responsiveness, and a decreased temperature dependence of the response speed.

EXAMPLE 16

A blank cell was prepared in the same manner as in Example 15 by using a 2% aqueous solution of polyvinyl alcohol resin (PVA-117, available from Kuraray K.K.) instead of the 1.5%-solution of polyimide resin precursor in dimethylacetoamide on each electrode plate. A ferroelectric liquid crystal device was prepared by filling the blank cell with the liquid crystal composition N prepared in Example 15. The liquid crystal device was subjected to measurement of optical response time in the same manner as in Example 7. The results are shown below.

|  | 10° C. | 25° C. | 40° C. |
|---|---|---|---|
| Response time (μsec) | 563 | 293 | 161 |

| Ex. Comp. No. | Structural formula | wt. parts |
|---|---|---|
| 1-21 | C$_{11}$H$_{23}$—[benzoxazole]—[phenyl]—C$_8$H$_{17}$ | 4 |
| 1-101 | C$_6$H$_{13}$O—[benzoxazole]—[phenyl]—OC$_6$H$_{13}$ | 2 |
| 1-113 | C$_8$H$_{17}$O—[benzoxazole]—[phenyl]—OCH$_2$*CH(F)C$_6$H$_{13}$ | 2 |
| Composition L | | 92 |

A ferroelectric liquid crystal device was prepared in the same manner as in Example 7 except that the above liquid crystal composition N was used, and the device

EXAMPLE 17

A blank cell was prepared in the same manner as in Example 15 except for omitting the SiO₂ layer to form an alignment control layer composed of the polyimide resin layer alone on each electrode plate. A ferroelectric liquid crystal device was prepared by filling the blank cell with the liquid crystal composition N prepared in Example 15. The liquid crystal device was subjected to measurement of optical response time in the same manner as in Example 7. The results are shown below.

|  | 10° C. | 25° C. | 40° C. |
| --- | --- | --- | --- |
| Response time (μsec) | 549 | 288 | 159 |

As is apparent from the above Examples 16 and 17, also in the cases of different device structures, the devices containing the ferroelectric liquid crystal composition N according to the present invention respectively provided a remarkably improved operation characteristic at a lower temperature and also a decreased temperature-dependence of the response speed similar to those in Example 15.

As described hereinabove, according to the present invention, there is provided a mesomorphic compound which can effectively be applied to a liquid crystal device utilizing ferroelectricity when the compound per se assumes a chiral smectic phase. Further, there is also provided a liquid crystal composition containing the compound and assuming a chiral smectic phase, whereby a liquid crystal device comprising the composition can be operated by utilizing ferroelectricity of the composition. The present invention provides a liquid crystal device using such a composition which shows a good switching characteristic, an improved low-temperature operation characteristic and a decreased temperature-dependence of response speed. The present invention further provides a display apparatus and a display method which employ such a device as a display unit, whereby good display characteristics can be obtained in combination with a light source, a drive circuit, etc.

What is claimed is:

1. A mesomorphic compound represented by the following formula (I):

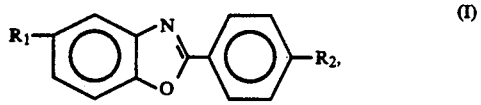

(I)

wherein R₁ and R₂ independently denote an alkyl group or alkoxyl group each having 4–16 carbon atoms optionally substituted with fluorine or alkoxy group, —CN or —CF₃.

2. A mesomorphic compound according to claim 1, wherein R₁ and R₂ independently denote any one of the following groups (i) to (v):
   (i) an n-alkyl group or n-alkoxy group each having 4–16 carbon atoms;
   (ii)

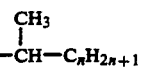

wherein l is 0 or 1, m is an integer of 0–6 and n is an integer of 1–8;
   (iii)

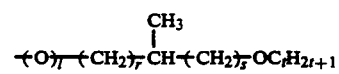

wherein l is 0 or 1, r is an integer of 0–6, s is 0 or 1, and t is an integer of 1–12;
   (iv)

wherein l is 0 or 1, and x is an integer of 4–14; and
   (v) —CN or —CF₃.

3. A liquid crystal composition, comprising: at least two mesomorphic compounds, at least one of said mesomorphic compounds being of the following formula (I):

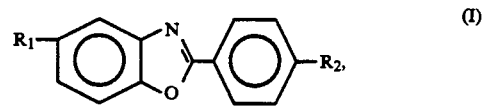

wherein R₁ and R₂ independently denote an alkyl group or alkoxyl group each having 4–16 carbon atoms optionally substituted with alkoxy group, halogen, —CN or —CF₃.

4. A liquid crystal composition according to claim 3, which comprises 1–80 wt. % of a mesomorphic compound of the formula (I).

5. A liquid crystal composition according to claim 3, which comprises 1–60 wt. % of a mesomorphic compound of the formula (I).

6. A liquid crystal composition according to claim 3, which comprises 1–40 wt. % of a mesomorphic compound of the formula (I).

7. A liquid crystal composition according to claim 3, which assumes a chiral smectic phase.

8. A liquid crystal composition according to claim 3, wherein R₁ and R₂ in the formula (I) independently denote any one of the following groups (i) to (v):
   (i) an n-alkyl group or n-alkoxy group each having 4–16 carbon atoms;
   (ii)

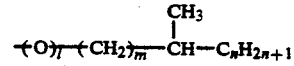

wherein l is 0 or 1, m is an integer of 0–6 and n is an integer of 1–8;
   (iii)

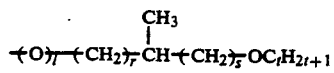

wherein l is 0 or 1, r is an integer of 0–6, s is 0 or 1, and t is an integer of 1–12;

(iv)

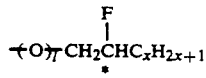

wherein l is 0 or 1 and x is an integer of 4–14; and (v) F, Cl, Br, —CN or —CF$_3$.

9. A liquid crystal device, comprising a pair of electrode plates and a liquid crystal composition according to claim 3 disposed between the electrode plates.

10. A liquid crystal device according to claim 9, wherein R$_1$ and R$_2$ in the formula (I) independently denote any one of the following groups (i) to (v):

(i) an n-alkyl group or n-alkoxy group each having 4–16 carbon atoms;

(ii)

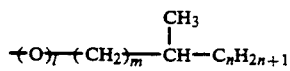

wherein l is 0 or 1, m is an integer of 0–6 and n is an integer of 1–8;

(iii)

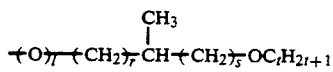

wherein l is 0 or 1, r is an integer of 0–6, s is 0 or 1, and t is an integer of 1–12;

(iv)

wherein l is 0 or 1 and x is an integer of 4–14; and (v) F, Cl, Br, —CN or —CF$_3$.

11. A liquid crystal device according to claim 9, which further comprises an insulating alignment control layer.

12. A liquid crystal device according to claim 11, wherein the insulating alignment control layer has been subjected to rubbing.

13. A display apparatus comprising a liquid crystal device according to claim 9, and voltage application means for driving the liquid crystal device.

14. A display apparatus according to claim 13, wherein R$_1$ and R$_2$ in the formula (I) independently denote any one of the following groups (i) to (v):

(i) an n-alkyl group or n-alkoxy group each having 4–16 carbon atoms;

(ii)

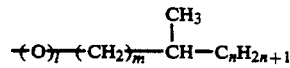

wherein l is 0 or 1, m is an integer of 0–6 and n is an integer of 1–8;

(iii)

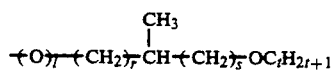

wherein l is 0 or 1, r is an integer of 0–6, s is 0 or 1, and t is an integer of 1–12;

(iv)

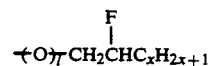

wherein l is 0 or 1 and x is an integer of 4–14; and (v) F, Cl, Br, —CN or —CF$_3$.

15. A display apparatus according to claim 13, which further comprises a drive circuit.

16. A display apparatus according to claim 13, which further comprises a light source.

* * * * *

UNITED STATES PATENT AND TRADEMARK OFFICE
CERTIFICATE OF CORRECTION

PATENT NO. : 5,318,720

DATED : June 7, 1994

INVENTOR(S) : TAKAO TAKIGUCHI, ET AL.

It is certified that error appears in the above-identified patent and that said Letters Patent is hereby corrected as shown below:

ON TITLE PAGE

Item: [56] References Cited, under FOREIGN PATENT DOCUMENTS: "0005188  4/1979" should read --0005188  11/1979--.

COLUMN 1

Line 38, "for driving," should be deleted.

COLUMN 18

Line 39, "—OC—," should read -- —OC—, OCH$_2$— or —CH$_2$O—,--.
            ‖                        ‖
            O                        O

COLUMN 20

Line 16, "bond," should read --bond, —CO—,--.
                                    ‖
                                    O

COLUMN 33

Line 21, "g" should read --q--.

COLUMN 34

Line 25, "SbnO$_2$" should read --SnO$_2$--.
Line 31, "tion" should read --tion.--.

COLUMN 45

Line 22, "wee" should read --were--.

UNITED STATES PATENT AND TRADEMARK OFFICE
CERTIFICATE OF CORRECTION

PATENT NO. : 5,318,720
DATED : June 7, 1994
INVENTOR(S) : TAKAO TAKIGUCHI, ET AL.

It is certified that error appears in the above-identified patent and that said Letters Patent is hereby corrected as shown below:

COLUMN 64

Line 23, "or—$CF_3$." should read -- or —$CF_3$.--.

Signed and Sealed this

Twenty-second Day of November, 1994

Attest:

BRUCE LEHMAN

Attesting Officer  Commissioner of Patents and Trademarks